(12) United States Patent
Potyrailo et al.

(10) Patent No.: US 9,638,653 B2
(45) Date of Patent: May 2, 2017

(54) HIGHLY SELECTIVE CHEMICAL AND BIOLOGICAL SENSORS

(71) Applicant: General Electric Company, Schenectady, NY (US)

(72) Inventors: Radislav Alexandrovich Potyrailo, Niskayuna, NY (US); Cheryl Margaret Surman, Albany, NY (US); Andrew Arthur Paul Burns, Schenectady, NY (US); Nandini Nagraj, Clifton Park, NY (US)

(73) Assignee: General Electricity Company, Schenectady, NY (US)

( * ) Notice: Subject to any disclaimer, the term of this patent is extended or adjusted under 35 U.S.C. 154(b) by 0 days.

(21) Appl. No.: 14/710,299

(22) Filed: May 12, 2015

(65) Prior Publication Data

US 2016/0223484 A1     Aug. 4, 2016

Related U.S. Application Data

(62) Division of application No. 14/031,951, filed on Sep. 19, 2013, now Pat. No. 9,037,418, which is a division
(Continued)

(51) Int. Cl.
*G01N 27/02* (2006.01)
*G01N 33/487* (2006.01)
*G01N 33/483* (2006.01)

(52) U.S. Cl.
CPC .......... *G01N 27/026* (2013.01); *G01N 27/02* (2013.01); *G01N 33/483* (2013.01); *G01N 33/48792* (2013.01)

(58) Field of Classification Search
CPC .. G01N 27/02; G01N 27/122; G01N 33/0004; G01N 27/3278; G01N 33/48792;
(Continued)

(56) References Cited

U.S. PATENT DOCUMENTS

D218,009 S     7/1970  Bosack
D219,617 S    12/1970  Swift
(Continued)

FOREIGN PATENT DOCUMENTS

AU     2015268746 A1    7/2016
CN        1363844 A     8/2002
(Continued)

OTHER PUBLICATIONS

Persaud et al., "Analysis of Discrimination Mechanisms in the Mammalian Olfactory System Using a Model Nose", Nature, vol. No. 299, pp. 352-355, Sep. 23, 1982.
(Continued)

*Primary Examiner* — John H Le
(74) *Attorney, Agent, or Firm* — Jean K. Testa; Fletcher Yoder, P.C.

(57) ABSTRACT

Methods and sensors for selective fluid sensing are provided. Each sensor includes a resonant inductor-capacitor-resistor (LCR) sensor that is coated with a sensing material. In order to collect data, an impedance spectrum is acquired over a relatively narrow frequency range, such as the resonant frequency range of the LCR circuit. A multivariate signature may be calculated from the acquired spectrum to discern the presence of certain fluids and/or fluid mixtures. The presence of fluids is detected by measuring the changes in dielectric, dimensional, resistance, charge transfer, and other changes in the properties of the materials employed by observing the changes in the resonant electronic properties of the circuit. By using a mathematical procedure, such as principal components analysis (PCA) and others, multiple fluids and mixtures can be detected in the presence of one another, even in a high humidity environment or an environment wherein one or more fluids has a substantially
(Continued)

higher concentration (e.g. 10×, 1,000,000×) compared to other components in the mixture.

18 Claims, 21 Drawing Sheets

Related U.S. Application Data of application No. 12/942,732, filed on Nov. 9, 2010, now Pat. No. 8,542,023.

(58) Field of Classification Search
CPC ......... G01N 2291/0256; G01N 27/021; G01N 29/036; G01G 3/16; G06K 19/0717; G06K 19/07749
USPC ....... 702/19, 23, 25, 30; 324/71.1, 602, 633, 324/652, 655; 73/31.05, 64.53; 310/360; 340/10, 41
See application file for complete search history.

(56) References Cited

U.S. PATENT DOCUMENTS

| | | |
|---|---|---|
| 3,675,121 A | 7/1972 | Thompson |
| 3,778,706 A | 12/1973 | Thompson |
| 3,927,369 A | 12/1975 | Billeter et al. |
| 4,096,385 A | 6/1978 | Marett |
| 4,273,636 A | 6/1981 | Shimada et al. |
| 4,275,364 A | 6/1981 | Skatvold |
| 4,372,164 A | 2/1983 | Brown et al. |
| 4,553,434 A | 11/1985 | Spaargaren |
| 4,728,892 A | 3/1988 | Vinegar et al. |
| 4,820,989 A | 4/1989 | Vail, III |
| 4,844,097 A | 7/1989 | Bellhouse et al. |
| 4,876,512 A | 10/1989 | Kroeger et al. |
| 4,882,542 A | 11/1989 | Vail, III |
| 4,887,455 A | 12/1989 | Payne et al. |
| 4,887,798 A | 12/1989 | Julius |
| 4,922,745 A | 5/1990 | Rudkin et al. |
| 4,941,958 A | 7/1990 | Byers |
| 4,965,522 A | 10/1990 | Hazen et al. |
| 4,996,490 A | 2/1991 | Scott et al. |
| 5,010,301 A | 4/1991 | Leung et al. |
| 5,025,346 A | 6/1991 | Tang et al. |
| 5,059,790 A | 10/1991 | Klainer et al. |
| 5,089,780 A | 2/1992 | Megerle |
| 5,157,338 A | 10/1992 | Motherbaugh et al. |
| 5,208,165 A | 5/1993 | Law et al. |
| 5,241,364 A | 8/1993 | Kimura |
| 5,260,569 A | 11/1993 | Kimura |
| 5,306,644 A | 4/1994 | Myerholtz et al. |
| 5,344,547 A | 9/1994 | Vlasov et al. |
| 5,421,983 A | 6/1995 | Slack et al. |
| 5,443,985 A | 8/1995 | Lu et al. |
| 5,497,140 A | 3/1996 | Tuttle |
| 5,543,722 A | 8/1996 | Suzuki et al. |
| 5,591,896 A | 1/1997 | Lin |
| 5,592,040 A | 1/1997 | Yamamoto |
| 5,607,566 A | 3/1997 | Brown et al. |
| 5,646,592 A | 7/1997 | Tuttle |
| 5,672,319 A | 9/1997 | Eisum |
| 5,744,902 A | 4/1998 | Vig |
| 5,751,475 A | 5/1998 | Ishiwata et al. |
| 5,754,055 A | 5/1998 | McAdoo et al. |
| 5,785,181 A | 7/1998 | Quartararo, Jr. |
| 5,786,595 A | 7/1998 | Herron et al. |
| 5,817,943 A | 10/1998 | Welles, II et al. |
| 5,831,439 A | 11/1998 | Suenram et al. |
| 5,840,168 A | 11/1998 | Chaniotakis et al. |
| 5,874,047 A | 2/1999 | Schoening et al. |
| 5,961,923 A | 10/1999 | Nova et al. |
| 6,025,725 A | 2/2000 | Gershenfeld et al. |
| 6,025,783 A | 2/2000 | Steffens, Jr. |
| 6,111,520 A | 8/2000 | Allen et al. |
| 6,166,546 A | 12/2000 | Scheihing et al. |
| 6,189,656 B1 | 2/2001 | Morgenstern et al. |
| 6,192,753 B1 | 2/2001 | Czarnek |
| 6,204,764 B1 | 3/2001 | Maloney |
| 6,278,379 B1 | 8/2001 | Allen et al. |
| 6,287,765 B1 | 9/2001 | Cubicciotti |
| 6,359,444 B1 | 3/2002 | Grimes |
| 6,360,585 B1 | 3/2002 | Potyrailo et al. |
| 6,398,931 B1 | 6/2002 | Burchette et al. |
| 6,399,375 B2 | 6/2002 | Vajta |
| 6,406,668 B1 | 6/2002 | Dordick et al. |
| 6,461,872 B1 | 10/2002 | Sivavec et al. |
| 6,471,838 B1 | 10/2002 | Igel et al. |
| 6,506,346 B1 | 1/2003 | Monro |
| 6,532,834 B1 | 3/2003 | Pinto et al. |
| 6,544,193 B2 | 4/2003 | Abreu |
| 6,586,946 B2 | 7/2003 | Hefti et al. |
| 6,614,229 B1 | 9/2003 | Clark et al. |
| 6,657,429 B1 | 12/2003 | Goldfine et al. |
| 6,672,512 B2 | 1/2004 | Bridgelall |
| 6,676,903 B2 | 1/2004 | Potyrailo et al. |
| 6,730,201 B1 | 5/2004 | Kuhlman et al. |
| 6,751,557 B1 | 6/2004 | Shehab et al. |
| 6,771,074 B2 | 8/2004 | Zou et al. |
| 6,773,926 B1 | 8/2004 | Freund et al. |
| 6,780,307 B2 | 8/2004 | Kidwell |
| 6,782,736 B1 | 8/2004 | Hammer |
| 6,804,544 B2 | 10/2004 | Van Antwerp et al. |
| 6,818,450 B2 | 11/2004 | Eaton et al. |
| 6,864,801 B2 | 3/2005 | Tabanou et al. |
| 6,891,383 B2 | 5/2005 | Nicholson et al. |
| 6,911,818 B2 | 6/2005 | Julius |
| 6,953,520 B2 | 10/2005 | Yengoyan et al. |
| 7,017,404 B1 | 3/2006 | Kain |
| 7,031,560 B2 | 4/2006 | Lelong-Feneyrou et al. |
| 7,034,660 B2 | 4/2006 | Watters et al. |
| 7,038,470 B1 | 5/2006 | Johnson |
| 7,040,139 B2 | 5/2006 | Sunshine |
| 7,113,125 B2 | 9/2006 | Le Sesne |
| 7,125,382 B2 | 10/2006 | Zhou et al. |
| 7,126,013 B2 | 10/2006 | Heeney et al. |
| 7,168,310 B2 | 1/2007 | Al-Ruwaili |
| 7,171,312 B2 | 1/2007 | Steinthal et al. |
| 7,178,416 B2 | 2/2007 | Whelan et al. |
| 7,204,128 B1 | 4/2007 | Liu et al. |
| 7,252,010 B2 | 8/2007 | Ohta et al. |
| 7,276,916 B2 | 10/2007 | Hammer |
| 7,293,450 B2 | 11/2007 | Liu et al. |
| 7,317,989 B2 | 1/2008 | DiFoggio et al. |
| 7,335,336 B1 | 2/2008 | Kim |
| 7,343,800 B2 | 3/2008 | Harman et al. |
| 7,350,367 B2 | 4/2008 | Matsiev et al. |
| 7,434,457 B2 | 10/2008 | Goodwin et al. |
| 7,445,143 B2 | 11/2008 | Pang et al. |
| 7,449,893 B1 | 11/2008 | Tsironis |
| 7,455,108 B2 | 11/2008 | Jenkins et al. |
| 7,456,744 B2 | 11/2008 | Kuhns |
| 7,466,041 B2 | 12/2008 | Urman |
| 7,481,771 B2 | 1/2009 | Fonseca et al. |
| 7,483,743 B2 | 1/2009 | Mann et al. |
| 7,486,495 B1 | 2/2009 | Diederichs et al. |
| 7,495,454 B2 | 2/2009 | Rivera |
| 7,523,647 B2 | 4/2009 | Scott |
| 7,562,557 B2 | 7/2009 | Bennett et al. |
| 7,569,810 B1 | 8/2009 | Troxler et al. |
| 7,629,167 B2 | 12/2009 | Hodge et al. |
| 7,677,307 B2 | 3/2010 | Vasques et al. |
| 7,691,329 B2 | 4/2010 | Potyrailo et al. |
| 7,697,574 B2 | 4/2010 | Suematsu et al. |
| 7,808,235 B2 | 10/2010 | Rollins et al. |
| 7,812,609 B2 | 10/2010 | Martinez et al. |
| 7,814,786 B2 | 10/2010 | Woodard |
| 7,948,380 B2 | 5/2011 | Kuhns et al. |
| 7,948,385 B2 | 5/2011 | Potyrailo et al. |
| 7,958,772 B2 | 6/2011 | Permuy et al. |
| 7,969,307 B2 | 6/2011 | Peeters |
| 8,018,342 B2 | 9/2011 | Monk et al. |
| 8,063,648 B2 | 11/2011 | Nilsson et al. |
| 8,111,143 B2 | 2/2012 | Tong et al. |

(56) References Cited

U.S. PATENT DOCUMENTS

| | | |
|---|---|---|
| 8,154,389 B2 | 4/2012 | Rowland et al. |
| 8,155,891 B2 | 4/2012 | Kong et al. |
| 8,159,347 B2 | 4/2012 | Potyrailo et al. |
| 8,184,290 B2 | 5/2012 | Hertens et al. |
| 8,190,394 B2 | 5/2012 | Davis et al. |
| 8,215,166 B2 | 7/2012 | Cunningham et al. |
| 8,232,091 B2 | 7/2012 | Maltezos et al. |
| 8,246,910 B2 | 8/2012 | Dhirani et al. |
| 8,261,618 B2 | 9/2012 | Engle et al. |
| 8,318,099 B2 | 11/2012 | Potyrailo et al. |
| 8,342,242 B2 | 1/2013 | Roddy et al. |
| 8,429,985 B2 | 4/2013 | Furlong |
| 8,452,716 B2 | 5/2013 | Howley et al. |
| 8,468,871 B2 | 6/2013 | Potyrailo et al. |
| 8,508,368 B2 | 8/2013 | Potyrailo et al. |
| 8,547,110 B2 | 10/2013 | Kesil et al. |
| 8,643,388 B2 | 2/2014 | Hedges |
| 8,676,436 B2 | 3/2014 | Raimarckers et al. |
| 8,710,973 B2 | 4/2014 | Schneider et al. |
| 8,732,938 B2 | 5/2014 | Kolosov et al. |
| 8,736,425 B2 | 5/2014 | Potyrailo |
| 8,833,145 B2 | 9/2014 | Fischer et al. |
| 8,933,706 B1 | 1/2015 | Karlquist |
| 8,952,708 B2 | 2/2015 | Nikolenko |
| 9,074,966 B2 | 7/2015 | Sanderlin et al. |
| 9,536,122 B2 | 1/2017 | Potyrailo |
| 2001/0045355 A1 | 11/2001 | Gephart et al. |
| 2002/0050929 A1 | 5/2002 | Parrotta et al. |
| 2002/0081231 A1 | 6/2002 | Shapiro et al. |
| 2002/0089356 A1 | 7/2002 | Perrott et al. |
| 2002/0149466 A1 | 10/2002 | Sunshine et al. |
| 2002/0173040 A1 | 11/2002 | Potyrailo et al. |
| 2002/0177232 A1 | 11/2002 | Melker et al. |
| 2002/0197725 A1 | 12/2002 | Eaton et al. |
| 2003/0053936 A1 | 3/2003 | Potyrailo et al. |
| 2003/0154031 A1 | 8/2003 | Potyrailo et al. |
| 2003/0179024 A1 | 9/2003 | Montagnana |
| 2003/0232223 A1 | 12/2003 | Leddy et al. |
| 2004/0051154 A1 | 3/2004 | Yamakawa et al. |
| 2004/0113790 A1 | 6/2004 | Hamel et al. |
| 2004/0125442 A1 | 7/2004 | Yun et al. |
| 2004/0155667 A1 | 8/2004 | Kesil et al. |
| 2004/0189487 A1 | 9/2004 | Hoefel et al. |
| 2004/0219523 A1 | 11/2004 | Stanton et al. |
| 2004/0227682 A1 | 11/2004 | Anderson |
| 2004/0248315 A1 | 12/2004 | Klein et al. |
| 2005/0022581 A1 | 2/2005 | Sunshine |
| 2005/0058460 A1 | 3/2005 | Wang |
| 2005/0081374 A1 | 4/2005 | Eckstein et al. |
| 2005/0093760 A1 | 5/2005 | Rochelle et al. |
| 2005/0161405 A1 | 7/2005 | Holland |
| 2005/0193832 A1 | 9/2005 | Tombs et al. |
| 2005/0199731 A9 | 9/2005 | Empedocles et al. |
| 2006/0014172 A1 | 1/2006 | Muller et al. |
| 2006/0020427 A1 | 1/2006 | Kahn et al. |
| 2006/0055531 A1 | 3/2006 | Cook et al. |
| 2006/0081471 A1 | 4/2006 | Kidwell |
| 2006/0133720 A1 | 6/2006 | Hochberg et al. |
| 2006/0141469 A1 | 6/2006 | Rossier et al. |
| 2006/0198760 A1 | 9/2006 | Potyrailo et al. |
| 2006/0205093 A1 | 9/2006 | Prins |
| 2006/0210440 A1 | 9/2006 | Potyrailo et al. |
| 2006/0238349 A1 | 10/2006 | Hu et al. |
| 2006/0265150 A1 | 11/2006 | Hu et al. |
| 2007/0029195 A1 | 2/2007 | Li et al. |
| 2007/0064839 A1 | 3/2007 | Luu |
| 2007/0084277 A1 | 4/2007 | Steinsiek |
| 2007/0085686 A1 | 4/2007 | Oz |
| 2007/0090926 A1 | 4/2007 | Potyrailo et al. |
| 2007/0090927 A1 | 4/2007 | Potyrailo et al. |
| 2007/0111222 A1 | 5/2007 | Chasin et al. |
| 2007/0131418 A1 | 6/2007 | Barrow et al. |
| 2007/0148670 A1 | 6/2007 | O'Malley |
| 2007/0176773 A1 | 8/2007 | Smolander et al. |
| 2007/0236338 A1 | 10/2007 | Maruyama |
| 2007/0241890 A1 | 10/2007 | Yoshioka |
| 2008/0061965 A1 | 3/2008 | Kuhns et al. |
| 2008/0090926 A1 | 4/2008 | Kang et al. |
| 2008/0093219 A1 | 4/2008 | Goldberg et al. |
| 2008/0116908 A1 | 5/2008 | Potyrailo et al. |
| 2008/0135614 A1 | 6/2008 | Werner et al. |
| 2008/0142366 A1 | 6/2008 | Tamirisa et al. |
| 2008/0157901 A1 | 7/2008 | Matekovits et al. |
| 2008/0177150 A1 | 7/2008 | Ii et al. |
| 2008/0179197 A1 | 7/2008 | Wu |
| 2008/0180249 A1 | 7/2008 | Butler et al. |
| 2008/0184787 A1 | 8/2008 | Coates |
| 2008/0191859 A1 | 8/2008 | Tiek et al. |
| 2008/0236814 A1 | 10/2008 | Roddy |
| 2008/0280374 A1 | 11/2008 | Potyrailo et al. |
| 2009/0035856 A1 | 2/2009 | Galliher et al. |
| 2009/0039864 A1 | 2/2009 | Gordon |
| 2009/0087862 A1 | 4/2009 | Carter et al. |
| 2009/0095073 A1 | 4/2009 | Fukumura et al. |
| 2009/0104707 A1 | 4/2009 | Wang et al. |
| 2009/0120169 A1 | 5/2009 | Chandler et al. |
| 2009/0204250 A1 | 8/2009 | Potyrailo et al. |
| 2009/0215646 A1 | 8/2009 | Anslyn et al. |
| 2009/0256679 A1 | 10/2009 | Potyrailo et al. |
| 2009/0265037 A1 | 10/2009 | Bassa |
| 2009/0278685 A1 | 11/2009 | Potyrailo et al. |
| 2009/0289776 A1 | 11/2009 | Moore et al. |
| 2009/0308155 A1 | 12/2009 | Zhang |
| 2010/0021993 A1 | 1/2010 | Wang et al. |
| 2010/0042338 A1 | 2/2010 | Giurgiutiu et al. |
| 2010/0051266 A1 | 3/2010 | Roddy et al. |
| 2010/0059221 A1 | 3/2010 | Vannuffelen et al. |
| 2010/0075405 A1 | 3/2010 | Broadley |
| 2010/0102004 A1 | 4/2010 | Holland |
| 2010/0138267 A1 | 6/2010 | Vittal et al. |
| 2010/0153323 A1 | 6/2010 | Hennessy et al. |
| 2010/0231407 A1* | 9/2010 | Carr ............... G06K 19/0723 |
| | | 340/691.1 |
| 2010/0250170 A1 | 9/2010 | Kalinin et al. |
| 2010/0261226 A1 | 10/2010 | Niazi |
| 2010/0280788 A1 | 11/2010 | Bohan et al. |
| 2010/0295558 A1 | 11/2010 | Eberheim et al. |
| 2011/0006878 A1 | 1/2011 | Nyffeler et al. |
| 2011/0006900 A1 | 1/2011 | Nyffeler et al. |
| 2011/0012736 A1 | 1/2011 | Potyrailo et al. |
| 2011/0018649 A1 | 1/2011 | David et al. |
| 2011/0022318 A1 | 1/2011 | Zhao et al. |
| 2011/0029156 A1 | 2/2011 | Vernacchia et al. |
| 2011/0045601 A1 | 2/2011 | Gryska et al. |
| 2011/0051775 A1 | 3/2011 | Ivanov et al. |
| 2011/0101996 A1* | 5/2011 | Potyrailo ............... G01D 21/00 |
| | | 324/655 |
| 2011/0117538 A1 | 5/2011 | Niazi |
| 2011/0152706 A1 | 6/2011 | Christopherson et al. |
| 2011/0152750 A1 | 6/2011 | Dacey, Jr. et al. |
| 2011/0156177 A1 | 6/2011 | Merz |
| 2011/0160681 A1 | 6/2011 | Dacey, Jr. et al. |
| 2011/0221667 A1 | 9/2011 | Lee |
| 2011/0248825 A1 | 10/2011 | Hamel et al. |
| 2011/0263036 A1 | 10/2011 | Blauw et al. |
| 2011/0282540 A1 | 11/2011 | Armitage et al. |
| 2011/0283821 A1 | 11/2011 | Ober et al. |
| 2012/0001730 A1 | 1/2012 | Potyrailo et al. |
| 2012/0025526 A1 | 2/2012 | Luo et al. |
| 2012/0053881 A1 | 3/2012 | Schulz et al. |
| 2012/0161787 A1 | 6/2012 | Potyrailo et al. |
| 2012/0231504 A1 | 9/2012 | Niazi |
| 2012/0258441 A1 | 10/2012 | Gebauer et al. |
| 2012/0265036 A1 | 10/2012 | Estes et al. |
| 2012/0289757 A1 | 11/2012 | Boyden et al. |
| 2013/0041334 A1 | 2/2013 | Prioleau et al. |
| 2013/0060112 A1 | 3/2013 | Pryor et al. |
| 2013/0182819 A1 | 7/2013 | Dvorkin et al. |
| 2013/0285677 A1 | 10/2013 | Hammer |
| 2014/0019067 A1 | 1/2014 | Potyrailo et al. |
| 2014/0095102 A1 | 4/2014 | Potyrailo et al. |
| 2014/0182362 A1 | 7/2014 | Potyrailo et al. |
| 2014/0305194 A1 | 10/2014 | Surman et al. |

(56) References Cited

U.S. PATENT DOCUMENTS

| | | | |
|---|---|---|---|
| 2015/0185173 | A1 | 7/2015 | Potyrailo et al. |
| 2015/0233887 | A1 | 8/2015 | Surman et al. |
| 2016/0187277 | A1 | 6/2016 | Potyrailo et al. |

FOREIGN PATENT DOCUMENTS

| | | |
|---|---|---|
| CN | 1532372 A | 9/2004 |
| CN | 2809215 Y | 8/2006 |
| CN | 1865966 A | 11/2006 |
| CN | 101022760 A | 8/2007 |
| CN | 101057124 A | 10/2007 |
| CN | 201000455 Y | 1/2008 |
| CN | 101988574 A | 3/2011 |
| CN | 102022264 A | 4/2011 |
| CN | 102422330 A | 4/2012 |
| CN | 203923208 U | 11/2014 |
| EP | 2498076 A1 | 9/2012 |
| GB | 793953 A | 4/1958 |
| JP | 5774097 A | 5/1982 |
| JP | 59116855 U | 8/1984 |
| JP | 59160746 A | 9/1984 |
| JP | 0381659 A | 4/1991 |
| JP | 06160317 A | 6/1994 |
| JP | 06194333 A | 7/1994 |
| JP | 6086057 U | 12/1994 |
| JP | 0773282 A | 3/1995 |
| JP | 07120423 A | 5/1995 |
| JP | 08509549 A | 10/1996 |
| JP | 09292453 A | 11/1997 |
| JP | 10504388 A | 4/1998 |
| JP | 2000111547 A | 4/2000 |
| JP | 2001502791 A | 2/2001 |
| JP | 2002125206 A | 4/2002 |
| JP | 2003503011 A | 1/2003 |
| JP | 2003506706 A | 2/2003 |
| JP | 2003161637 A | 6/2003 |
| JP | 2005156569 A | 6/2005 |
| JP | 2006516721 A | 7/2006 |
| JP | 2007516509 A | 6/2007 |
| JP | 2008129009 A | 6/2008 |
| JP | 2008236617 A | 10/2008 |
| JP | 2008298565 A | 12/2008 |
| JP | 2009092633 A | 4/2009 |
| JP | 2009538433 A | 11/2009 |
| JP | 2009540292 A | 11/2009 |
| JP | 2011258627 A | 9/2016 |
| WO | 9845779 A1 | 10/1998 |
| WO | 0055583 A1 | 9/2000 |
| WO | 0060120 A2 | 10/2000 |
| WO | 0173380 A1 | 10/2001 |
| WO | 0212129 A1 | 2/2002 |
| WO | 0223176 A1 | 3/2002 |
| WO | 03050529 A1 | 6/2003 |
| WO | 2004032191 A2 | 4/2004 |
| WO | 2007075619 A1 | 7/2007 |
| WO | 2007101992 A1 | 9/2007 |
| WO | 2008082654 A2 | 7/2008 |
| WO | 2013057630 A1 | 4/2013 |
| WO | 2015090358 A1 | 6/2015 |
| WO | 2015128050 A1 | 9/2015 |

OTHER PUBLICATIONS

Sen et al., "Frequency Dependent Dielectric and Conuctivity Response of Sedimentary Rocks", Journal of Microwave Power, vol. No. 18, Issue No. 1, pp. 95-105, 1983.

Raythatha et al., "Dielectric Properties of Clay Suspensions in MHz to GHz Range", Journal of Colloid and Interface Science, vol. No. 109, Issue No. 2, pp. 301-309, Feb. 1986.

Ward et al., "In Situ Interfacial Mass Detection with Piezoelectric Transducers", Science, vol. No. 249, Issue No. 1972, pp. 1000-1007, Aug. 31, 1990.

Shi et al., "Capacitance-Based Instrumentation for Multi-Interface Level Measurement", Measurement Science and Technology, vol. No. 2, Issue No. 10, pp. 923-933, 1991.

Wise et al., "Microfabrication Techniques for Integrated Sensors and Microsystem", Science, vol. No. 254, pp. 1335-1342, 1991.

Mullen et al., "Trace Detection of Ionic Species with Surface Enhanced Raman Spectroscopy", Spectroscopy, vol. No. 7, pp. 24-32, 1992.

Ervin et al., "Development of a Fiber-Optic Sensor for Trace Metal Detection in Aqueous Environments", Applied Dptics, vol. No. 32, Issue No. 22, pp. 4287-4290, Aug. 1, 1993.

Agar et al., "Energy Absorption Probes Control Oily-Water Discharges", Hydrocarbon Processing, vol. No. 72, Issue No. 8, Aug. 1, 1993.

Wensink, "Dielectric Properties of Wet Soils in the Frequency Range 1-3000 MHz", Geophysical Prospecting, vol. No. 41, Issue No. 6, pp. 671-696, Aug. 1993.

Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.

Pal, "Techniques for Measuring the Composition (Oil and Water Content) of Emulsions—Astate of the Art Review", Colloids and Surfaces: A Physicochemical and Engineering Aspects, vol. No. 84, Issue No. 2-3, pp. 141-193, 1994.

Isaksen et al., "A Capacitance-Based Tomography System for Interface Measurement in Separation Vessels", Measurement Science and Technology, vol. No. 5, Issue No. 10, pp. 1262-1271, Jun. 1994.

Yang et al., "A Multi-Interface Level Measurement System using a Segmented Capacitance Sensor for Oil Separators", Measurement Science and Technology, pp. 1177-1180, Jul. 19, 1994.

Amrani et al., "High-Frequency Measurements of Conducting Polymers: Development of a New Technique for Sensing Volatile Chemicals", http://iopscience.iop.org/0957-0233/6/10/010; 8 pages, 1995.

Legin et al "Development and Analytical Evaluation of a Multisensor System for Water Quality Monitoring", Sensors and Actuators B: Chemical, vol. No. 27, Issue No. 1-3, pp. 377-379, Jun. 1995.

Nicolaou et al., "Radiofrequency Encoded Combinatorial Chemistry", Angewandte Chemie International Edition, vol. No. 34, pp. 2289-2291, 1995.

Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, 1995.

Hutzler et al., "Measurement of Foam Density Profiles Using AC Capacitance", Europhysics Letters, vol. No. 31, Issue No. 8, pp. 497-502, Sep. 10, 1995.

Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.

Malinowska et al., "Enhanced Electrochemical Performance of Solid-State Ion Sensors Based on Silicone Rubber Membranes", Sensors and Actuators B: Chemical, vol. No. 43, Issue No. 1-3, pp. 851-854, Jul. 1996.

Amrani et al., "Multi-frequency Measurements of Organic Conducting Polymers for Sensing of Gases and Vapours", Sensors and Actuators B: Chemical, vol. No. 33, Issue No. 1-3, pp. 137-141, Jul. 1996.

Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.

Chinowski et al., "Experimental Data from a Trace Metal Sensor Combining Surface Plasmon Resonance with Anodic Stripping Voltametry", Sensors and Actuators B: Chemical, vol. No. 35, Issue No. 1-3, pp. 37-43, Sep. 1996.

Josse et al., "AC-Impedance-Based Chemical Sensors for Organic Solvent Vapors", Sensors and Actuators B: Chemical, vol. No. 36, Issue No. 1-3, pp. 363-369, Oct. 1996.

(56) References Cited

OTHER PUBLICATIONS

Kress-Rogers, "Handbook of Biosensors and Electronic Noses: Medicine, Food, and the Environment", CRC Press, 20 pages, Oct. 24, 1996 (summary).
Santamarina et al., "Dielectric Permittivity of Soils Mixed With Organic and Inorganic Fluids (0.02ghz to 1.30 GHz)", Journal of Environmental and Engineering Geophysics, vol. No. 2, Issue No. 1, pp. 37-51, 1997.
Hammond et al., "An Acoustic Automotive Engine Oil Quality Sensor", Solid State Sensors and Actuators, vol. 2, pp. 1343-1346, Jun. 1997.
Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.
Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.
Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.
Wohltjen et al., "Colloidal Metal-Insulator-Metal Ensemble Chemiresistor", Anal.Chem, vol. No. 70, Issue No. 14, pp. 2856-2859, 1998.
Chyan et al., "Ultrapure Water Quality Monitoring by a Silicon-Based Potentiometric Sensor"Analyst, vol. No. 125, Issue No. 1, pp. 175-178, 1999.
Homola et al., "Surface Plasmon Resonance Sensors: Review", Sensors and Actuators B: Chemical, vol. No. 54, Issue No. 1-2, pp. 3-15, Jan. 25, 1999.
Jaworski et al., "A Capacitance Probe for Interface Detection in Oil and Gas Extraction Plant", Measurement of Science and Technology, vol. No. 10, Issue No. 3, pp. L15-L20, Jan. 1999.
Amrani et al., "Multi-Frequency Interrogation Technique Applied to Conducting Polymer Gas and Odour Sensors", vol. 146, pp. 95-101, Mar. 1999.
Schuller et al., "Advanced Profile Gauge for Multiphase Systems", 1st World Congress on Industrial Process Tomography, Buxton, Greater Manchester, Apr. 14-17, 1999.
Asskildit et al., "New Measuring Sensor for Level Detection in Subsea Separators", ABB Review, pp. 11-17, Apr. 1999.
Ishida et al., "Effects of pH on Dielectric Relaxation of Montmorillonite, Allophane, and Imogolite Suspensions, Colloid and Interface Science", ScienceDirect, vol. No. 212, Issue No. 1, pp. 152-161, Apr. 1999.
Legin et al., "The Features of the Electronic Tongue in Comparison with the Characterstics of the Discrete Ion Selective Sensor", Sensors and Actuators B: Chemical, vol. No. 58, Issue No. 1-3, pp. 464-468, Sep. 21, 1999.
Artmann, "Electronic Identification Systems: State of the Art and their Further Development", Computers and Electronics in Agriculture, vol. No. 24, Issue No. 1-2, pp. 5-26, Nov. 1999.
Jurs et al., "Computational Methods for the Analysis of Chemical Sensor Array Data from Volatile Analytes", Chemical Reviews, vol. No. 100, Issue No. 7, pp. 2649-2678, 2000.
McQuade et al., "Conjugated Polymer-Based Chemical Sensors", Chem. Rev, vol. No. 100, Issue No. 7, pp. 2537-2574, 2000.
Vlasov et al., "Electronic Tongue—New Analytical Tool for Liquid Analysis on the basis of Non-Specific Sensors and Methods of Pattern Recognition", Sensors and Actuators B: Chemical, vol. No. 65, Issue No. 1-3, pp. 235-236, Jun. 30, 2000.
Rakow et al., "A Colorimetric Sensor Array for Odour Visualization", Nature, vol. No. 406, pp. 710-713, Aug. 17, 2000.
Taton et al., "Scanometric DNA Array Detection with Nanoparticle Probes", Science, vol. No. 289, Issue No. 5485, pp. 1757-1760, Sep. 8, 2000.
Shirakawa, "The Discovery of Polyacetylene Film: The Dawning of an Era of Conducting Polymers", Angewandte Chemie International Edition, vol. No. 40, Issue No. 14, pp. 2574-2580, Jul. 16, 2001.
Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.
Kaya, "A Electrical Spectroscopy of Kaolin and Bentonite Slurries", Turkish Journal of Engineering and Environmental Sciences, vol. No. 25, pp. 345-354, 2001.
Lee, "Increase Oil Production and Reduce Chemical Usage through Separator Level Measurement by Density Profiling", ISA TECH/EXPO Technology Update Conference Proceedings, vol. No. 416, pp. 321-328, 2001.
Macdiarmid, "Synthetic Metals: A Novel Role for Organic Polymers", Angewandte Chemie International Edition, vol. No. 40, pp. 2581-2590, 2001.
Heeger, "Semiconducting and Metallic Polymers: The Fourth Generation of Polymeric Materials", The Journal of Physical Chemistry B, vol. No. 105, Issue No. 36, pp. 8475-8491, 2001.
Mourzina et al., "Development of Multisensor Systems based on Chalcogenide Thin Film Chemical Sensors for the Simulataneous Multicomponent Analysis of Metal Ions in Complex Solutions", Electrochimica Acta, vol. No. 47, Issue No. 1-2, pp. 251-258, Sep. 1, 2001.
Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.
Akyildiz et al., "Wireless Sensor Networks: A survey", Computer Networks, vol. No. 38, pp. 393-422, 2002.
Harpster et al., "A Passive Humidity Monitoring System for In-Situ Remote Wireless Testing of Micropackages", Microelectromechanical System, vol. No. 11, Issue No. 1, pp. 61-67, 2002.
Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, 2002.
Janata et al., "Electrochemical Sensors and their Impedances: A Tutorial", Critical Reviews in Analytical Chemistry, vol. No. 32, Issue No. 2, pp. 109-120, 2002.
Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, 2002.
Alary et al.,"Subsea Water Separation: A Cost-effective Solution for Ultra Deep Water Production", 17th World Petroleum Congress, Rio de Janeiro, Brazil, Sep. 1-5, 2002.
Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.
Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.
Fauveau et al., "Guided-Wave RADAR helps Level-Detection in Harsh Settings Control Engineering", Control Engineering, vol. No. 50, Issue No. 3, pp. 16, Mar. 2003.
Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 15, 2003.
Grimes et al., "Resonance Sensors: A Critical Review Sensors", Analytical Chemistry, vol. No. 75, Issue No. 8, pp. 1868-1879, Apr. 15, 2003.
De Borba et al., "Determination of Sodium at Low Ng/L Concentrations in Simulated Power Plant Waters by Ion Chromatography", Journal of Chromatography, vol. No. 995, Issue No. 1-2, pp. 143-152, May 2, 2003.
Sakharov et al., "Liquid Level Sensor using Ultrasonic Lamb Waves", Ultrasonics, vol. No. 41, Issue No. 4, pp. 319-322, Jun. 2003.
Kumar et al., "Investigation into the Interaction between Surface-Bound Alkylamines and Gold Nanoparticles", Langmuir, vol. No. 19, Issue No. 15, pp. 6277-6282, 2003.

(56) References Cited

OTHER PUBLICATIONS

Potyrailo et al., "Fluorescence Spectroscopy and Multivariate Spectral Descriptor Analysis for High-Throughput Multiparameter Optimization of Polymerization Conditions of Combinatorial 96-Microreactor Arrays", Journal of Combinatorial Chemistry, vol. No. 5, Issue No. 1, pp. 8-17, 2003.
Mabic et al., "Quality Adjustment of Treated Water in an Experimental Detection", GIT Labor-Fachzeitschrift, vol. No. 47, pp. 724-727, 2003.
Pasquale, "Mechanical Sensors and Actuators", Sensors and Actuators, A: Physical, vol. No. 106, Issue No. 1-3, pp. 142-148, 2003.
Chopra et al., "Selective Gas Detection Using a Carbon Nanotube Sensor", Applied Physics Letters, vol. No. 83, pp. 2280-2282, 2003.
Janata et al., "Conducting Polymers in Electronic Chemical Sensors", Nature Materials, vol. No. 2, pp. 19-24, 2003.
Bauer et al, "Resonant Nanocluster Technology—From Optical Coding and High Quality Security Features to Biochips", Nanotechnology, vol. No. 14, Issue No. 12, pp. 1289-1311, Nov. 4, 2003.
Joseph et al., "Chemiresistor Coatings from Pt- And Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15, 2004.
Shamsipur et al., "New Macrocyclic Diamides as Neutral Ionophores for Highly Selective and Sensitive PVC-Membrane Electrodes for Be2+ Ion", Electroanalysis, vol. No. 16, Issue No. 4, pp. 282-288, Mar. 2004.
Fransen, "New Control System Detects Desalter Problems before Upsets Occur", Agar Corporation, Prepared for presentation at The Aiche 2004 Spring National Meeting, Apr. 2004.
Bennett et al., "Monitoring the Operation of an Oil/Water Separator using Impedance Tomography", Minerals Engineering, vol. No. 17, Issue No. 5, pp. 605-614, May 2004.
Pavlov et al., "Aptamer-Functionalized Au Nanoparticles for the Amplified Optical Detection of Thrombin", Journal of be American Chemical Society, vol. No. 126, Issue No. 38, pp. 11768-11769, 2004.
Varma et al., "High-Speed Label-Free Detection by Spinning-Disk Micro-Interferometry", Biosensors and Bioelectronics, vol. No. 19, Issue No. 11, pp. 1371-1376, 2004.
Seyfried et al., "Measurement of Soil Water Content with a 50-MHz Soil Dielectric Sensor", Soil Science Society of America, vol. No. 68, Issue No. 2, pp. 394-403, 2004.
Want et al., "Enabling Ubiquitous Sensing with RFID", Computer, vol. No. 37, Issue No. 4, pp. 84-86, 2004.
Briglln et al., "Detection of Organic Mercaptan Vapors using Thin Films of Alkylamine-Passivated Gold Nanocrystals", Langmuir, vol. No. 20, Issue No. 2, pp. 299-305, 2004.
Ikenishi et al., "The Dielectric Characteristics of Agricultural Land for On-site and Real Time Measurement", SICE 2004 Annual Conference on, IEEE Xplore, vol. No. 2, pp. 1489-1492, Aug. 4-6, 2004.
Thomas et al., "Conjugated Polymer Sensors: Design Principles Towards Enhanced Versatility", Report No. A035334, 2 pages, Dec. 2004.
Rose et al., "Sensitivity Gains in Chemosensing by Lasing Action in Organic Polymers", Nature, vol. 434, pp. 376-879, Apr. 14, 2005.
Holstad et al., "Scattered Gamma Radiation Utilized for Level Measurements in Gravitational Separators", IEEE Sensors, vol. No. 5, Issue No. 2, pp. 175-182, Apr. 2005.
Cheung et al., "Impedance Spectroscopy Flow Cytometry: on-Chip Label-Free cell Differentiation", Cytometry A, vol. No. 65, Issue No. 2, pp. 124-132, Jun. 2005.
Jang et al., "Chemical Sensors Based on Highly Conductive Poly(3,4-Ethylene- Dioxythiophene) Nanorods", Advanced Materials, vol. No. 17, Issue No. 13, pp. 1616-1620, Jul. 2005.
Rakow et al., "Molecular Recognition and Discrimination of Amines with a Colorimetric Array", Angewandte Chemie, vol. No. 44, Issue No. 29, pp. 4528-4532, Jul. 18, 2005.

Zhang et al., "Colorimetric Sensor Array for Organics in Water", Journal of the American Chemical Society, vol. No. 127, Issue No. 33, pp. 11548-11549, 2005.
Jaworski et al., "Measurements of Oil-Water Separation Dynamics in Primary Separation Systems Using Distributed Capacitance Sensors", Flow Measurement and Instrumentation, vol. No. 16, Issue No. 2-3, pp. 113-127, 2005.
Buhrdorf et al., "Multiparameteric Oil Condition Sensor Based on the Tuning Fork Technology for Automotive Applications", Book chapter in Advanced Microsystems for Automotive Applications, pp. 289-298, 2005.
Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, 2005.
Chuang et al., "Embeddable Wireless Strain Sensor Based on Resonant RF Cavities", Review of Scientific Instruments, vol. No. 20, pp. 1-7, Sep. 2005.
Bang et al., "A Novel Electrochemical Detection Method for Aptamer Biosensors", Biosensors and Bioelectronics, vol. No. 21, Issue No. 6, pp. 863-870, Dec. 15, 2005.
Locklin et al., "Effect of Morphology on Organic Thin Film Transistor Sensors", Analytical and Bioanalytical Chemistry, vol. No. 384, Issue No. 2, pp. 336-342, Jan. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 2006.
Casanella et al., "Oil-water Interface Level Sensor Based on an Electrode Array", Instrumentation and Measurement Technology Coference, Sorrento, Italy, pp. 710-713, Apr. 24-27, 2006.
Lange et al., "Measuring Biomolecular Binding Events with a Compact Disc Player Device", Angewandte Chemie International Edition, vol. No. 45, pp. 270-273, 2006.
Swiech et al., "Dielectric Properties of Synthetic Oil Sands", Society of Petroleum Engineers—SPE Heavy Oil Conference Canada, vol. No. 1, pp. 238-248, 2013.
Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.
US Final Rejection issued in connection with corresponding U.S. Appl. No. 12/325,653 on Aug. 8, 2013.
Unofficial English Translation of Japanese Office Action issued in connection with corresponding JP Application No. 2011-538590 on Oct. 8, 2013.
PCT Search Report and Written Opinion issued in connection with corresponding PCT Application No. PCT/SE2013/050671 on Nov. 18, 2013.
PCT Search Report and Written Opinion issued in connection with corresponding PCT Application No. PCT/US2013/058932 on Dec. 12, 2013.
PCT Search Report and Written Opinion issued in connection with corresponding PCT Application No. PCT/US2013/058898 on Dec. 18, 2013.
Unofficial English Translation of Chinese Office Action issued in connection with corresponding CN Application No. 201180031959.6 on Dec. 26, 2013.
US Non-Final Rejection issued in connection with corresponding U.S. Appl. No. 12/977,568 on Jan. 16, 2014.
PCT Search Report and Written Opinion issued in connection with corresponding PCT Application No. PCT/US2013/055983 on Jan. 27, 2014.
US Non-Final Rejection issued in connection with corresponding U.S. Appl. No. 12/827,623 on Jan. 30, 2014.
European Search Report and Opinion issued in connection with corresponding EP Application No. 11801238A on Mar. 5, 2014.
US Non-Final Rejection issued in connection with corresponding U.S. Appl. No. 12/325,653 on Mar. 17, 2014.
A copy of PCT Search Report and Written Opinion issued in connection with corresponding PCT Application No. PCT/SE2013/051590 on May 6, 2014.

(56) References Cited

OTHER PUBLICATIONS

PCT Search Report and Written Opinion issued in connection with corresponding PCT Application No. PCT/SE2013/051589 on May 6, 2014.
US Non-Final Rejection issued in connection with corresponding U.S. Appl. No. 13/630,939 on Aug. 11, 2014.
US Non-Final Rejection issued in connection with corresponding U.S. Appl. No. 14/031,965 on Aug. 26, 2014.
Soleimani et al., "Base Oil Oxidation Detection using Novel Chemical Sensors and Impedance Spectroscopy Measurements", Sensors and Actuators B: Chemical, vol. No. 199, pp. 247-258, Aug. 2014.
US Final Rejection issued in connection with corresponding U.S. Appl. No. 12/325,653 on Sep. 12, 2014.
Toledo et al., "Application of Quartz Tuning Forks and Extensional Microresonators for Viscosity and Density Measurements in Oil/Fuel Mixtures", Microsystem Technologies, vol. No. 20, Issue No. 4, pp. 945-953, 2014.
US Non-Final Rejection issued in connection with corresponding U.S. Appl. No. 13/484,674 on Nov. 3, 2014.
US Non-Final Rejection issued in connection with corresponding U.S. Appl. No. 13/558,499 on Dec. 4, 2014.
US Non-Final Rejection issued in connection with corresponding U.S. Appl. No. 13/630,954 on Dec. 15, 2014.
US Non-Final Rejection issued in connection with corresponding U.S. Appl. No. 13/729,800 on Dec. 19, 2014.
US Final Rejection issued in connection with corresponding U.S. Appl. No. 13/630,939 on Jan. 28, 2015.
US Non-Final Rejection issued in connection with corresponding U.S. Appl. No. 13/630,739 on Feb. 25, 2015.
Unofficial English Translation of Chinese Office Action issued in connection with corresponding CN Application No. 201180032850.4 on Mar. 2, 2015.
Unofficial English Translation of Japanese Office Action issued in connection with corresponding JP Application No. 2013518325 on Mar. 24, 2015.
Unofficial English Translation of Chinese Office Action issued in connection with corresponding CN Application No. 201110461799.0 on Mar. 30, 2015.
Zhu et al.,"An Integrated Lubricant Oil Conditioning Sensor Using Signal Multiplexing", Journal of Micromechanics and Micro engineering, vol. No. 25, Issue No. 1, pp. 1-12, 2015.
Unofficial English Translation of Japanese Office Action issued in connection with corresponding JP Application No. 2013-518328 on Apr. 7, 2015.
US Non-Final Rejection issued in connection with corresponding U.S. Appl. No. 13/729,851 on Apr. 28, 2015.
US Non-Final Rejection issued in connection with corresponding U.S. Appl. No. 13/630,587 on Jun. 2, 2015.
US Final Rejection issued in connection with corresponding U.S. Appl. No. 13/630,739 on Jun. 4, 2015.
US Non-Final Rejection issued in connection with corresponding U.S. Appl. No. 13/838,884 on Jun. 17, 2015.
PCT Search Report and Written Opinion issued in connection with corresponding PCT Application No. PCT/US2015/027482 on Jul. 15, 2015.
Unofficial English Translation of Japanese Notice of Allowance issued in connection with corresponding JP Application No. 2011-258627 on Aug. 4, 2015.
Taiwan Office Action issued in connection with corresponding TW Application No. 100146015 on Aug. 6, 2015.
US Non-Final Rejection issued in connection with corresponding U.S. Appl. No. 13/630,939 on Sep. 14, 2015.
Unofficial English Translation of Japanese Grant of Patent issued in connection with corresponding JP Application No. 2013518325 on Sep. 15, 2015.
US Non-Final Rejection issued in connection with corresponding U.S. Appl. No. 13/538,570 on Oct. 22, 2015.
European Search Report and Opinion issued in connection with corresponding EP Application No. 118012343 on Oct. 28, 2015.
Unofficial English Translation of Chinese Office Action issued in connection with corresponding CN Application No. 201380043615.6 on Nov. 9, 2015.
US Non-Final Rejection issued in connection with corresponding U.S. Appl. No. 12/824,436 on Dec. 2, 2015.
Potyrailo et al., "Selective Detection of Chemical Species in Liquids and Gases using Passive Radio-Frequency Identification (RFID) Sensors", Proc. Transducers, pp. 1650-1653, 2009.
McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, 2009.
Sweden Office Action issued in connection with corresponding SE Application No. 0702495-3 on Jan. 26, 2009.
Jaworski et al., "On-line Measurement of Separation Dynamics in Primary Gas/Oil/Water Separators: Challenges and Technical Solutions—A review", Petroleum Science and Engineering, vol. No. 68, pp. 47-59, 2009.
Potyrailo et al., "Combinatorial Screening of Polymeric Sensing Materials Using RFID Sensors",Journal of combinatorial Chemistry, vol. No. 11, Issue No. 4, pp. 598-603, 2009.
Westafer et al., "Functionalization of High Frequency SAW RFID Devices for Ozone Dosimetry", IEEE Sensors, pp. 1747-1752, Oct. 25-28, 2009.
Sweden Office Action issued in connection with corresponding SE Application No. 0702495-3 on Sep. 29, 2009.
PCT Search Report and Written Opinion issued in connection with corresponding PCT Application No. PCT/SE2009/051346 on Mar. 15, 2010.
US Non-Final Rejection issued in connection with corresponding U.S. Appl. No. 11/560,476 on Apr. 5, 2010.
Potyrailo et al. "Integration of Passive Multivariable RFID Sensors into Single-Use Biopharmaceutical Manufacturing Components", RFID, 2010 IEEE International, pp. 1-7, Apr. 2010.
Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.
Hong et al., "Development of a Micro Liquid-Level Sensor for Harsh Environments using a Periodic Heating Technique", Measurement Science and Technology, vol. No. 21, Issue No. 10, 2010.
Potyrailo et al., "Passive Radio Frequency Identification (RFID) Chemical Sensors for Homeland Security Applications", In Wiley Handbook of Science and Technology for Homeland Security, vol. No. 1, pp. 523-544, 2010.
Nang et al., "Flexible Chemiresistor Sensors: Thin film Assemblies of Nanoparticles on a Polyethylene Terephthalate Substrate", Journal of Materials Chemistry, vol. No. 20, pp. 907-915, 2010.
Alexander et al., "Optimization of Interdigitated Electrode (IDE) Arrays for Impedance Based Evaluation of Hs 578T Cancer Cells", Journal of Physics: Conference Series, vol. No. 24, Issue No. 1, pp. 1-4, 2010.
Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.
Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, 2010.
Cho et al., "Capacitive Sensor for Automotive Engine Oil Degradation using Wireless Network", International Symposium on Advanced Packaging Materials: Microtech, APM '10 , pp. 88-91, 2010.
De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, 2010.
Bianchi et al., "Model of an Interdigitated Microsensor to Detect and Quantify Cells Flowing in a Test Chamber", 6th annual COMSOL Conference Paris, pp. 1-5, Nov. 2010.

(56) References Cited

OTHER PUBLICATIONS

Suresh et al., "Piezoelectric Based Resonant Mass Sensor using Phase Measurement", Measurement, vol. No. 44, Issue No. 2, pp. 320-325, Feb. 2011.

Perez et al., "Low-Cost Oil Quality Sensor Based on Changes in Complex Permittivity", Sensors, vol. No. 11, pp. 10675-10690, 2011.

Potyrailo et al. "RFID Sensors as the Common Sensing Plafform for Single-Use Biopharmaceutical Manufacturing", Measurement Science and Technology, vol. No. 22, 2011.

Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2011.

Owenier et al., "Dielectric Permittivity of Geologic Materials at Different Water Contents—Measurements with an Impedance Analyzer", 6th International Workshop on Advanced Ground Penetrating Radar (IWAGPR), pp. 1-5, Jun. 22-24, 2011.

Potyrailo et al., "Multivariable Passive RFID Vapor Sensors: Pilot-Scale Manufacturing and Laboratory Evaluation", IEEE International Conference on RFID, Poster 52, 2011.

US Non-Final Rejection issued in connection with corresponding U.S. Appl. No. 12/424,016 on Jul. 12, 2011.

Guan et al.,"Application of Dielectric Spectroscopy for Engine Lubricating Oil Degradation Monitoring", Sensors and Actuators A: Physical, vol. No. 168, Issue No. 1, pp. 22-29, Jul. 2011.

Wang et al., "Impedance Analysis for Lateral Field Excited Acoustic Wave Sensors", Sensors and Actuators B: Chemical, vol. No. 156, Issue No. 2, pp. 969-975, Aug. 2011.

Sen et al., "Evaluation of Sensor Arrays for Engine Oils Using Artificial Oil Alteration", Proceedings of SPIE 8066, Smart Sensors Actuators and MEMS V, 2011.

Latif et al., "Conductometric Sensors for Monitoring Degradation of Automotive Engine Oil", Sensors, vol. No. 11, Issue No. 9, pp. 8611-8625, Sep. 2011.

PCT Search Report and Written Opinion issued in connection with corresponding PCT Application No. PCT/SE2011/050748 on Oct. 5, 2011.

PCT Search Report and Written Opinion issued in connection with corresponding PCT Application No. PCT/SE2011/050818 on Oct. 24, 2011.

Potyrailo et al., "Materials and Transducers Toward Selective Wireless Gas Sensing", Chemical Reviews, vol. No. 111, Issue No. 11, pp. 7315-7354, Nov. 9, 2011.

Datla et al., "Wireless Distributed Computing: A Survey of Research Challenges", IEEE Communications Magazine, vol. No. 50, Issue No. 1, pp. 144-152, Jan. 2012.

Combined GB Search and Examination Report issued in connection with corresponding GB Application No. GB1121548.0 on Mar. 28, 2012.

Vasilyeva et al., "Differences in Behaviour of Adsorbed Water in Kaolinites and Montmorillonites in Temperature Range from −90° C. to +140° C. by Dielectric Spectroscopy", Physics: Conference Series, vol. No. 394, Issue No. 1, pp. 1-6, 2012.

Aghayan, "On-Line Monitoring of Engine Health through the Analysis of Contaminants in Engine Lubricant", The School of Graduate and Postdoctoral Studies The University of Western Ontario London, Ontario, Canada, pp. 1-273, 2012.

US Non-Final Rejection issued in connection with corresponding U.S. Appl. No. 12/824,436 on Aug. 8, 2012.

Fochtmann et al., "Optimization of the Lateral Field Excited Platform for Liquid Sensing Applications", Sensors and Actuators B: Chemical, vol. No. 170, pp. 95-103, Jul. 1, 2012.

US Non-Final Rejection issued in connection with corresponding U.S. Appl. No. 11/560,476 on Jul. 5, 2012.

Datla et al., "Wireless Distributed Computing in Cognitive Radio Networks", Ad Hoc Networks, vol. No. 10, Issue No. 05, pp. 845-857, Jul. 2012.

Unofficial English Translation of Japanese Office Action issued in connection with corresponding JP Application No. 2007291481 on Aug. 7, 2012.

US Non-Final Rejection issued in connection with corresponding U.S. Appl. No. 13/331,003 on Sep. 10, 2012.

US Notice of Allowance issued in connection with corresponding U.S. Appl. No. 12/424,016 on Sep. 28, 2012.

Chinese Office Action issued in connection with corresponding CN Application No. 200980149087.6 on Sep. 13, 2012.

US Non-Final Rejection issued in connection with corresponding U.S. Appl. No. 12/325,653 on Nov. 16, 2012.

US Non-Final Rejection issued in connection with corresponding U.S. Appl. No. 12/977,599 on Feb. 5, 2013.

US Final Rejection issued in connection with corresponding U.S. Appl. No. 12/824,436 on Feb. 6, 2013.

De Souza et al., "A Close Dielectric Spectroscopic Analysis of Diesel/Biodiesel Blends and Potential Dielectric Approaches for Biodiesel Content Assessment", Fuel, vol. No. 105, pp. 705-710, Mar. 2013.

Yang, "Sensors and Instrumentation for Monitoring and Control of Multi-Phase Separation", Measurement and Control, vol. No. 39, Issue No. 6, pp. 178-184, Jul. 2006.

Morris et al., "Wireless Sensor Array System for Combinatorial Screening of Sensor Materials", Combinatorial Methods and Informatics in Materials Science, vol. No. 894, pp. 219-224, 2006.

Yang et al., "Chemical Identification Using an Impedance Sensor Based on Dispersive Charge Transport", Applied Physics Letters, vol. No. 88, pp. 1-3, 2006.

Pejcic et al., "Impedance Spectroscopy: Over 35 Years of Electrochemical Sensor Optimization", Electrochimica Acta, vol. No. 51, Issue No. 28, pp. 6217-6229, Sep. 15, 2006.

Benini et al., "Wireless Sensor Networks: Enabling Technology for Ambient Intelligence", Microelectronics Journal, vol. No. 37, Issue No. 12, pp. 1639-1649, Dec. 2006.

Bai et al., "Gas Sensors Based on Conducting Polymers", Sensors (Basel), vol. No. 7, Issue No. 3, pp. 267-307, Mar. 2007.

Casanella et al., "Continuous Liquid Level Measurement Using a Linear Electrode Array", Measurement Science and Technology, vol. No. 18, Issue No. 7, pp. 178-184, May 9, 2007.

Liu et al., "Measurement of Density and Viscosity of Dodecane and Decane with a Piezoelectric Tuning Fork Over 298-448 K and 0.1-137.9 MPa", Sensors and Actuators A Physical, vol. No. 167, Issue No. 2, pp. 347-353, Jun. 2007.

Lu et al., "MEMS-Based Inductively Coupled RFID Transponder for Implantable Wireless Sensor Applications", IEEE Transactions on Magnetics, vol. No. 43, Issue No. 6, pp. 2412-2414, 2007.

Potyrailo et al., "Multianalyte Chemical Identification and Quantitation Using a Single Radio Frequency Identification Sensor", Analytical Chemistry, vol. No. 79, Issue No. 1, pp. 45-51, 2007.

Potyrailo et al., "Wireless Resonant Sensor Array for High-Throughput Screening of Materials", Review of Scientific Instruments, vol. No. 78, 2007.

Sugiyasu et al., "Conducting-Polymer-Based Chemical Sensors: Transduction Mechanisms", Bulletin of the Chemical Society of Japan, vol. No. 80, pp. 2074-2083, 2007.

Gutzeit, "Controlling Crude Unit Overhead Corrosion—Rules of Thumb for Better Crude Desalting", NACE International Corrosion Conference Series, pp. 075671-0756721, 2007.

Bai et al., "Gas sensor based conducting polymers", Sensors, vol. No. 7, pp. 267-307, 2007.

Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, 2007.

Armani et al., "Single-Molecule Detection with Optical Microcavities", Science, vol. No. 317, Issue No. 5839, pp. 783-787, Aug. 10, 2007.

Hempel et al., "5D-2 Application of a Portable RF Impedance Spectrum Analyzer for the Investigation of Lateral Field Excited Acoustic Wave Sensors in a Liquid Environment", Ultrasonics Symposium, pp. 373-376, 2007.

(56) References Cited

OTHER PUBLICATIONS

Li et al., "Chemosensory Performance of Molecularly Imprinted Fluorescent Conjugated Polymer Materials", Journal of the American Chemical Society, vol. No. 129, Issue No. 51, pp. 15911-15918, 2007.

Li et al., "Inkjet Printed Chemical Sensor Array Based on Polythiophene Conductive Polymers", Sensors and Actuators B, vol. No. 123, pp. 651-660, 2007.

Wang et al., "A New Method for On-line Monitoring of Brake Fluid Condition using an Enclosed Reference Probe", Measurement Science and Technology, vol. No. 18, Issue No. 11, pp. 3625-3635, 2007.

Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.

Wei et al., "Simple and Sensitive Aptamer-Based Colorimetric Sensing of Protein using Unmodified Gold Nanoparticle Probes", Chemical Communications, pp. 3735-3737, 2007.

Metzger et al., "Low-cost Weight-sensitive Foam to Monitor Product Availability on Retail Shelves", International conference on Pervasive Computing (Pervasive2007), pp. 268-279, 2007.

Hewitt, "Oil/Water Interface Control for Desalters", Petroleum Technology Quarterly 2007, vol. No. 12, Issue No. 5, pp. 75-78, 2007.

Hwili et al., "Multi-Modality Multi-Interface Level Measurement", Physics: Conference Series, vol. No. 76, Issue No. 1, pp. 1-6, 2007.

Wang et al., "A Gold Nanoparticle-Based Aptamer Target Binding Readout for ATP Assay", Advanced Materials, vol. No. 19, Issue No. 22, pp. 3943-3946, Nov. 2007.

Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.

Wang et al., "Aptamer Biosensor for Protein Detection using Gold Nanoparticles", Analytical Biochemistry, vol. No. 373, Issue No. 2, pp. 213-219, Feb. 15, 2008.

Wang et al., "Electrochemical Sensors for Clinic Analysis", Sensors (Basel), vol. No. 8, Issue No. 4, pp. 2043-2081, Apr. 2008.

Potyrailo et al., "Position-Independent Chemical Quantitation with Passive 13.56-Mhz Radio Frequency Identification (RFID) Sensors", Talanta, vol. No. 75, Issue No. 3, pp. 624-628, May 15, 2008.

Röck et al., "Electronic Nose: Current Status and Future Trends", Chemical Reviews, vol. No. 108, pp. 705-725, 2008.

Jimenez et al., "Surface Characterization of Clay Particles via Dielectric Spectroscopy", Annales Umcs, Chemistry, vol. No. 63, Issue No. 1, pp. 73-86, Jan. 2008.

Wang et al., "Sensors and Biosensors for the Determination of Small Molecule Biological Toxins", Sensors, vol. No. 8, Issue No. 9, pp. 6045-6054, 2008.

Metzger et al., "Flexible-Foam-Based Capacitive Sensor Arrays for Object Detection at Low Cost", Applied Physics Letters, vol. No. 92, Issue No. 1, 2008.

Zheng et al., "Resonance Impedance Sensing of Human Blood Cells", Sensors and Actuators A: Physical, vol. No. 145-146, pp. 29-36, 2008.

Potyrailo et al., "Modeling of Selectivity of Multi-Analyte Response of Passive Radio Frequency Identification (RFID) Sensors", 12th International Meeting on Chemical Sensors, Columbus, 2008.

Hempel et al., "Lateral Field Excited Quartz Crystal Resonator Sensors for Determination of Acoustic and Electrical Properties of Liquids", IEEE International Frequency Control Symposium, pp. 705-710, 2008.

Uid, "Ultrasonic Interface Level Detector", Christian Michelsen Research, 2008.

Capone et al., "Metal Oxide Gas Sensor Array for the Detection of Diesel Fuel in Engine Oil", Sensors and Actuators B: Chemical, vol. No. 131, pp. 125-133, 2008.

Diamond et al., "Wireless Sensor Networks and Chemo-/Biosensing", Chemical Reviews, vol. No. 108, Issue No. 2 , pp. 652-679, 2008.

Hatchett et al., "Composites of Intrinsically Conducting Polymers as Sensing Nanomaterials", Chemical Reviews, vol. No. 108, Issue No. 2, pp. 746-769, 2008.

Joo et al., "Chemical Sensors with Integrated Electronics", Chemical Reviews, vol. No. 108, Issue No. 2, pp. 638-651, 2008.

Kauffman et al., "Carbon Nanotube Gas and Vapor Sensors", Angewandte Chemie International Edition, vol. No. 47, pp. 6550-6570, 2008.

Li et al., "Chemical Sensing Using Nanostructured Polythiophene Transistors", Nano Letters, vol. No. 8, Issue No. 11, pp. 3563-3567, 2008.

Palacios et al., "Rational Design of a Minimal Size Sensor Array for Metal Ion Detection", Journal of the American Chemical Society, vol. No. 130, Issue No. 31, pp. 10307-10314, 2008.

Hwili et al., "A Single Rod Multi-Modality Multi-Interface Level Sensor using an AC Current Source", IEEE International Workshop on Imaging Systems and Techniques, Sep. 10-12, 2008.

Guan et al., "Engine Lubricating Oil Classification by SAE Grade and Source Based on Dielectric Spectroscopy Data", Analytica Chimica Acta, vol. No. 628, Issue No. 1, pp. 117-120, Oct. 17, 2008.

Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.

Misra, "Guide to Wireless Sensor Networks", Computer Communications and Networks, Jan. 1, 2009 (summary).

Ertl et al., "Interdigitated Impedance Sensors for Analysis of Biological Cells in Microfluidic Biochips", E & I Elektrotechnik und Informationstechnik, vol. No. 126, Issue No. 1, pp. 47-50, Feb. 2009.

Bauerle, "Study of Solid Electrolyte Polarization by a Complex Admittance Method", Journal of Physics and Chemistry of Solids, vol. No. 30, Issue No. 12, pp. 2657-2670, Dec. 1969.

Matsui, "Complex-Impedance Analysis for the Development of Zirconia Oxygen Sensors", Solid State Ionics, vol. No. 3-4, pp. 525-529, Aug. 1981.

Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.

Ghiotti et al., "Moisture Effects on Pure and Pd-Doped $SnO_2$ Thick Films Analysed by FTIR Spectroscopy and Conductance Measurements", Sensors and Actuators B: Chemical, vol. No. 25, Issue No. 1-3, pp. 520-524, Apr. 1995.

Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.

Amrani et al., "An Intelligent Gas Sensing System", Sensors and Actuators B: Chemical, vol. No. 44, Issue No. 1-3, pp. 512-516, Oct. 1997.

Basu et al., "Smart Sensing" of Oil Degradation and Oil Level Measurements in Gasoline Engines, SAE 2000 World Congress, Detroit, Michigan, 2000-01-1366, pp. 1-7, Mar. 6-9, 2000.

Foster et al., "Detection of Trace Levels of Water in Oil by Photoacoustic Spectroscopy", Sensors and Actuators B: Chemical, vol. No. 77, Issue No. 3, pp. 620-624, Jul. 10, 2001.

Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.

Grimes et al., "Wireless Magnetoelastic Resonance Sensors: A Critical Review", vol. No. 2, Issue No. 7, pp. 294-313, Jul. 23, 2002.

Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.

Finkenzeller, "RFID Handbook: Fundamentals and Applications in Contactless Smart Cards and Identification", John Wiley & Sons, Ltd, Second Edition, pp. 1-427, Jul. 21, 2003.

(56) References Cited

OTHER PUBLICATIONS

Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.
Barsoukov et al., "Impedance Spectroscopy: Theory, Experiment, and Applications", Second Edition, pp. 205-264, 2005.
Lvovich et al., "Impedance Characterization of Industrial Lubricants", Electrochimica Acta, vol. No. 51, Issue No. 3-9, pp. 1487-1496, Jan. 20, 2006.
Qing et al., "RFID Tag Antennas", Antennas for Portable Devices, John Wiley & Sons, Ltd, pp. 59-61; 65-69, Mar. 2007.
Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.
Surman et al., "Quantitation of Toxic Vapors in Variable Humidity Atmosphere Using Individual Passive Radio requency Identification (RFID) Sensors", 12th International Meeting on Chemical Sensors, Columbus, pp. 1-2, 2008.
Agoston et al., "A Concept of an Infrared Sensor System for Oil Condition Monitoring", Elektrotechnik & Informationstechnik, vol. No. 125, Issue No. 3, pp. 71-75, Mar. 2008.
Wudy et al., "Rapid Impedance Scanning QCM for Electrochemical Applications Based on Miniaturized Hardware and High-Performance Curve Fitting", Electrochimica Acta, vol. No. 53, Issue No. 22, pp. 6568-6574, Sep. 20, 2008.
Sacristan-Riquelme et al., "Low Power Impedance Measurement Integrated Circuit for Sensor Applications", Microelectronics Journal, vol. No. 40, Issue No. 1, pp. 177-184, Jan. 2009.
Niedermayer et al., "Yet Another Precision Impedance Analyzer (YAPIA)—Readout Electronics for Resonating Sensors", Sensors and Actuators A: Physical, vol. No. 156, Issue No. 1, pp. 245-250, Nov. 2009.
Mortier et al., "Chemistry and Technology of Lubricants", Third Edition, Springer, pp. 1-560, 2010.
Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.
Agilent Impedance Measurement Handbook, "A Guide to Measurement Technology and Techniques", 4th Edition, Agilent Technologies, pp. 1-140, Sep. 10, 2013.
Elzagzoug et al., "Condition Monitoring of High Voltage Transformer Oils Using Optical Chromaticity", Measurement Science and Technology, vol. No. 25, Issue No. 6, pp. 1-9, Jun. 2014.
US Non-Final Office Action issued in connection with related U.S. Appl. No. 13/331,003 on Sep. 10, 2014.
Hoja et al., "Miniaturized Impedance Analyzer Using AD5933", Lecture Notes on Impedance Spectroscopy, vol. No. 5, pp. 93-100, Feb. 17, 2015.
Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.
Simic, "Complex Impedance Measurement System for the Frequency Range from 5 kHz to 100 kHz", Key Engineering Materials, vol. No. 644, pp. 133-136, May 11, 2015.
Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.
Ghaffari et al., "A Wireless Multi-Sensor Dielectric Impedance Spectroscopy Platform", Sensors, vol. No. 15, Issue No. 9, pp. 23572-23588, Sep. 17, 2015.
Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.
Poseidon Systems, "Oil Quality Products", TRIDENT QM1100; TRIDENT QM2100; TRIDENT WM800, pp. 1-3, Retrieved from http://www.poseidonsys.com/products/oil-quality on Dec. 24, 2015.
Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.
Unofficial English Translation of Chinese Office Action issued in connection with related CN Application No. 201380050788.0 on Jan. 20, 2016.
PCT Search Report and Written opinion issued in connection with related PCT Application No. PCT/EP2015/075026 on Feb. 1, 2016.
AU Examination Report issued in connection with related AU Application No. 2013305814 on Jun. 10, 2016.
Eurasian Search Report issued in connection with related EA Application No. 201592216 on Aug. 4, 2016.
US Ex Parte Quayle Action issued in connection with related U.S. Appl. No. 14/532,168 on Aug. 4, 2016.
US Non-Final Office Action issued in connection with related U.S. Appl. No. 12/824,436 on Sep. 6, 2016.
Bret Dwayne Worden et al., filed Sep. 29, 2015, U.S. Appl. No. 14/869,038.
Radislav Alexandrovich Potyrailo et al., filed Sep. 25, 2015, U.S. Appl. No. 14/866,320.
Radislav Alexandrovich Potyrailo et al., filed Dec. 30, 2014, U.S. Appl. No. 14/585,690.
Cheryl Margaret Surman et al., filed May 2, 2014, U.S. Appl. No. 61/987,853.
Cheryl Margaret Surman et al., filed Dec. 22, 2015, U.S. Appl. No. 62/271,030.
Cheryl Margaret Surman et al., filed Apr. 27, 2015, U.S. Appl. No. 14/697,086.
Radislav Alexandrovich Potyrailo et al., filed Nov. 16, 2006, U.S. Appl. No. 11/560,476.
Radislav Aiexandrovich Potyrailo et al., filed Dec. 1, 2008, U.S. Appl. No. 12/325,653.
Cheryl Margaret Surman et al., filed Jun. 28, 2010, U.S. Appl. No. 12/824,436.
Radislav Alexandrovich Potyrailo et al., filed Jun. 30, 2010, U.S. Appl. No. 12/827,623.
Radislav Alexandrovich Potyrailo et al., filed Dec. 23, 2010, U.S. Appl. No. 12/977,568.
Radislav Alexandrovich Potyrailo et al., filed Dec. 20, 2011, U.S. Appl. No. 13/331,003.
Radislav Alexandrovich Potyrailo et al., filed Apr. 15, 2009, U.S. Appl. No. 12/424,016.
Radislav Alexandrovich Potyrailo et al., filed Jun. 29, 2012, U.S. Appl. No. 13/538,570.
Radislav Alexandrovich Potyrailo et al., filed Jul. 26, 2012, U.S. Appl. No. 13/558,499.
Radislav Alexandrovich Potyrailo et al., filed Sep. 28, 2012, U.S. Appl. No. 13/630,939.
Cheryl Margaret Surman et al., filed Sep. 28, 2012, U.S. Appl. No. 13/630,587.
Cheryl Margaret Surman et al., filed Sep. 28, 2012, U.S. Appl. No. 13/630,739.
Radislav Alexandrovich Potyrailo et al., filed Dec. 28, 2012, U.S. Appl. No. 13/729,800.
Radislav Alexandrovich Potyrailo et al., filed Dec. 28, 2012, U.S. Appl. No. 13/729,851.
Bret Dwayne Worden et al., filed Feb. 12, 2015, U.S. Appl. No. 14/421,245.
Radislav Alexandrovich Potyrailo et al., filed Dec. 23, 2010, U.S. Appl. No. 12/977,599.
Radislav Alexandrovich Potyrailo, filed Nov. 4, 2014, U.S. Appl. No. 14/532,168.
Radislav kexandrovich Potyrailo et al., filed Mar. 3, 2016, U.S. Appl. No. 15/060,193.
Radislav Alexandrovich Potyrailo et al., filed Jun. 7, 2016, U.S. Appl. No. 15/175,127.
Bret Worden et al., filed Dec. 18, 2015, U.S. Appl. No. 29/548,993.
Radislav A. Potyrailo, et al.; Development of Radio-Frequency Identification Sensors Based on Organic Electronic Sensing Materials for Selective Detection of Toxic Vapors; 2009 American Institute of Physics.

(56) References Cited

OTHER PUBLICATIONS

Radislav A. Potyrailo, et al.; Selective Quantitation of Vapors and their Mixtures using Individual Passive Multivariable RFID Sensors; 2010; pp. 22-28.
Radislav A. Potyrailo, et al.;RFID Sensors based on Ubiquitous Passive 13.56-MHz RFID Tags and Complex Impedance Detection; 2008 John Wiley& Sons, Ltd.
EE Lim Tan, et al.; A Wireless, Passive Sensor for Quantifying Packaged Food Quality; Sep. 5, 2007; 1747-1756.
Hendrick., "Cellulose Acetate Fibers with Fluorescing Nanoparticles for Anti-Counterfeiting Purposes", Erin Sue Hendrick, pp. 1-36, 2008.
Unofficial English Translation of Chinese Office Action issued in connection with related CN Application No. 212800701655.5 on Jul. 13, 2016.
European Search Report and Opinion issued in connection with related EP Application No. 09830658.2 on Sep. 16, 2016.
US Non-Final Rejection issued in connection with related U.S. Appl. No. 14/421,245 on Oct. 18, 2016.
Australian Examination Report issued in connection with related AU Application No. 2015268746 on Oct. 21, 2016.
US Supplemental Notice of Allowability issued in connection with related U.S. Appl. No. 14/532,168 on Oct. 25, 2016.
US Non-Final Rejection issued in connection with related U.S. Appl. No. 14/697,086 on Oct. 31, 2016.
Unofficial English Translation of Japanese Search Report issued in connection with related JP Application No. 2011258627 on Dec. 1, 2016.
Chinese Office Action, Issued Jul. 13, 2016, 20 Pages.

\* cited by examiner

| WATER VAPOR (PPM) | 1-OCTANOL DETECTION LIMIT (PPB) | WATER VAPOR OVERLOAD |
|---|---|---|
| 0 | 33 | 0 |
| 2807 | 30 | 92,312 |
| 5614 | 31 | 183,546 |
| 11,228 | 36 | 312,423 |
| 16,842 | 56 | 299,092 |

68

| WATER VAPOR (PPM) | 1-NONANOL DETECTION LIMIT (PPB) | WATER VAPOR OVERLOAD |
|---|---|---|
| 0 | 6 | 0 |
| 2807 | 6 | 454,348 |
| 5614 | 6 | 961,512 |
| 11,228 | 7 | 1,594,127 |
| 16,842 | 9 | 1,918,104 |

HIGHLY SELECTIVE CHEMICAL AND BIOLOGICAL SENSORS

CROSS REFERENCE TO RELATED APPLICATIONS

This application is a divisional of U.S. patent application Ser. No. 14/031,951, filed Sep. 19, 2013, which is a divisional of U.S. patent application Ser. No. 12/942,732, entitled "Highly Selective Chemical and Biological Sensors," filed Nov. 9, 2010, now U.S. Pat. No. 8,542,023, issued Sep. 24, 2013, which are herein incorporated by reference.

STATEMENT REGARDING FEDERALLY SPONSORED RESEARCH & DEVELOPMENT

This invention was made with Government support and funded in part by the National Institute of Environmental Health Sciences under Grant No. 1R01ES016569-01A1 and funded in part by the Air Force Research Laboratory under Contract No. FS8650-08-C-6869. The Government has certain rights in the invention.

BACKGROUND

The subject matter disclosed herein relates to chemical and biological sensors, and more particularly, to highly selective chemical and biological sensors.

Chemical and biological sensors are often employed in a number of applications were the detection of various vapors maybe used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications such as residential home monitoring, home land security in airports in different environmental and clinical settings and other public venues wherein detection of certain harmful and/or toxic vapors may be particularly useful.

One technique for sensing such environmental changes is by employing a sensor, such as an RFID sensor, coated with a particular sensing material. Also, sensors maybe arranged in an array of individual transducers which are coated with sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In certain applications multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response, complicates fabrication of the array.

Further, in many practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors.

Various embodiments disclosed herein may address one or more of the challenges set forth above.

BRIEF DESCRIPTION

In accordance with one embodiment, there is provided a sensor comprising a resonant inductor-capacitor-resistor (LCR) circuit and a sensing material disposed over the LCR circuit. The sensing material is configured to allow selective detection of at least six different analyte fluids or gases from an analyzed fluid or gas mixture.

In accordance with another embodiment, there is provided a method of detecting analytes in a fluid. The method comprises acquiring an impedance spectrum over a resonant frequency range of a resonant sensor circuit. The method further comprises calculating a multivariate signature from the acquired impedance spectrum.

In accordance with another embodiment, there is provided a method of detecting chemical or biological species in a fluid. The method comprises measuring a real part and an imaginary part of an impedance spectrum of a resonant sensor antenna coated with a sensing material. The method further comprises calculating at least six spectral parameters of the resonant sensor antenna coated with the sensing material. The method further comprises reducing the impedance spectrum to a single data point using multivariate analysis to selectively identify an analyte. The method further comprises determining one or more environmental parameters from the impedance spectrum.

In accordance with another embodiment, there is provided a sensor comprising a transducer and a sensing material disposed on the transducer. The transducer has a multivariate output to independently detect effects of different environmental parameters on the sensor. The sensing material has a preserved magnitude of response to an analyte over a broad concentration range of an interferent.

In accordance with another embodiment, there is provided a method for controlling selectivity of a sensor response of a sensor having an integrated circuit (IC) chip. The method comprises powering the IC chip to at least one power level to affect an impedance spectral profile of the sensor. The method further comprises collecting spectral parameters of the sensor response at the at least one power level. The method further comprises performing multivariate analysis of the spectral parameters. The method further comprises calculating values of environmental parameters to which the sensor is exposed from data produced by performing the multivariate analysis and using stored calibration coefficients.

In accordance with another embodiment, there is provided a method for controlling selectivity of a sensor response of an LCR sensor having a sensing material disposed thereon. The method comprises powering an inductor-resistor-capacitor (LCR) sensor to at least two power levels to affect at least one of the dipole moment, the dielectric constant, and the temperature of the sensing material. The method further comprises collecting spectral parameters of the sensor response at the at least two power levels. The method further comprises performing multivariate analysis of the spectral parameters from combined impedance spectral profiles of the LCR sensor at the different power levels. The method further comprises calculating values of environmental parameters to which the LCR sensor is exposed from data produced by performing the multivariate analysis.

DRAWINGS

These and other features, aspects, and advantages of the present invention will become better understood when the following detailed description is read with reference to the accompanying drawings in which like characters represent like parts throughout the drawings, wherein:

FIG. 11 illustrates tables relating to the comparative plots of FIG. 10, in accordance with embodiments of the invention;

DETAILED DESCRIPTION

Figure 1:
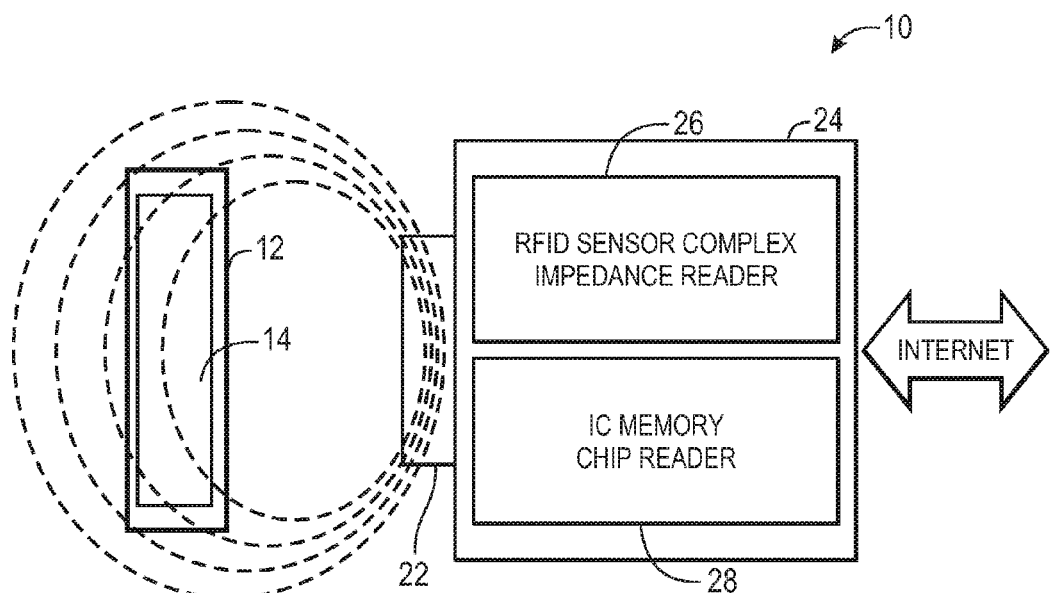
FIG. 1 illustrates a sensing system, in accordance with embodiments of the invention.

Embodiments disclosed herein provide methods and systems for selective vapor sensing wherein a single sensor is provided and is capable of detecting multiple vapors and/or mixtures of vapors alone, or in the presence of one another. The disclosed sensors are capable of detecting different vapors and mixtures even in a high humidity environment or an environment wherein one or more vapors has a substantially higher concentration (e.g. 10x) compared to other components in the mixture. Each sensor includes a resonant inductor-capacitor-resistor (LCR) sensor that is coated with a sensing material. Nonlimiting examples of LCR sensors include RFID sensors with an integrated circuit (IC) memory chip, RFID sensors with an IC chip, and RFID sensors without an IC memory chip (chipless RFID sensors). LCR sensors can be wireless or wired. In order to collect data, an impedance spectrum is acquired over a relatively narrow frequency range, such as the resonant frequency range of the LCR circuit. The technique further includes calculating the multivariate signature from the acquired spectrum and manipulating the data to discern the presence of certain vapors and/or vapor mixtures. The presence of vapors is detected by measuring the changes in dielectric, dimensional, charge transfer, and other changes in the properties of the materials employed by observing the changes in the resonant electronic properties of the circuit. By using a mathematical procedure, such as principal component analysis (PCA) and others, multiple vapors and mixtures can be detected in the presence of one another and in the presence of an interferent as further described below. Embodiments disclosed herein provide methods and systems for selective fluid sensing wherein a single sensor is provided and is capable of detecting multiple fluids and/or mixtures of fluids alone, or in the presence of one another.

To more clearly and concisely describe the subject matter of the claimed invention, the following definitions are provided for specific terms, which are used in the following description and the appended claims.

The term "fluids" includes gases, vapors, liquids, and solids.

The term "digital ID" includes all data stored in a memory chip of the RFID sensor. Nonlimiting examples of this data are manufacturer identification, electronic pedigree data, user data, and calibration data for the sensor.

The term "monitoring process" includes, but is not limited to, measuring physical changes that occur around the sensor. For example, monitoring processes including monitoring changes in a chemical, automotive, biopharmaceutical, food or beverage manufacturing process related to changes in physical, chemical, and/or biological properties of an environment around the sensor. Monitoring processes may also include those industry processes that monitor physical changes as well as changes in a component's composition or position. Nonlimiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.) Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady-state measurements of individual vapors and their mixtures.

The term "environmental parameters" is used to refer to measurable environmental variables within or surrounding a manufacturing or monitoring system. The measurable environmental variables comprise at least one of physical, chemical and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "analyte" includes any desired measured environmental parameter.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors". The appropriate selection of features is performed from all potential features that can be calculated from spectra. Multivariable spectral parameters are described in U.S. patent application Ser. No. 12/118,950 entitled "Methods and systems for calibration of RFID sensors", which is incorporated herein by reference.

The term "resonance impedance" or "impedance" refers to measured sensor frequency response around the resonance of the sensor from which the sensor "spectral parameters" are extracted.

The term "protecting material" includes, but is not limited to, materials on the LCR or RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another non-limiting example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper, polymeric, and inorganic films such as polyesters, polypropylene, polyethylene, polyethers, polycarbonate, polyethylene terepthalate, zeolites, metal-organic frameworks, and cavitands. The protecting material can be arranged between the transducer and sensing film to protect the transducer. The protecting material can be arranged on top of the sensing film which is itself is on top of the transducer to protect the sensing film and transducer. The protecting material on top of the sensing film which is itself is on top of the transducer can serve to as a filter material to protect the sensing film from exposure to gaseous or ionic interferences. Nonlimiting examples of filter materials include zeolites, metal-organic frameworks, and cavitands.

As used herein the term "sensing materials and sensing films" includes, but is not limited to, materials deposited onto a transducer's electronics module, such as LCR circuit components, an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the LCR or RFID sensor, the impedance sensor response changes as a function of pH. Thus, such an LCR or RFID sensor works as a pH sensor. When such a polyaniline film is deposited onto the LCR or RFID sensor for detection in gas phase, the impedance sensor response also changes upon exposure to basic (for example, $NH_3$) or acidic (for example HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black—polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaking into the liquid environment, the sensing materials are attached to the sensor surface using standard techniques, such as covalent bonding, electrostatic bonding and other standard techniques known to those of ordinary skill in the art.

The terms "transducer and sensor" are used to refer to electronic devices such as RFID devices intended for sensing. "Transducer" is a device before it is coated with a sensing or protecting film or before it is calibrated for sensing application. "Sensor" is a device typically after it is coated with a sensing or protecting film and after being calibrated for sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where a specific RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the complex impedance response, resonance peak position, peak width, peak height and peak symmetry of the impedance response of the sensor antenna, magnitude of the real part of the impedance, resonant frequency of the imaginary part of the impedance, antiresonant frequency of the imaginary part of the impedance, zero-reactance frequency, phase angle, and magnitude of impedance, and others as described in the definition of the term sensor "spectral parameters". The "RFID sensor" can have an integrated circuit (IC) memory chip attached to antenna or can have no IC memory chip. An RFID sensor without an IC memory chip is an LCR sensor. An LCR sensor is comprised of known components such as at least one inductor (L), at least one capacitor (C), and at least one resistor (R) to form an LCR circuit.

The term "single-use container" includes, but is not limited to, manufacturing or monitoring equipment, and packaging, which may be disposed of after use or reconditioned for reuse. Single-use packaging in the food industry includes but is not limited to food and drinks packaging, candy and confection boxes. Single-use monitoring components include, but are not limited to, single-use cartridges, dosimeters, and collectors. Single use manufacturing containers include, but are not limited to, single-use vessels, bags, chambers, tubing, connectors, and columns.

The term "writer/reader" includes, but is not limited to, a combination of devices to write and read data into the memory of the memory chip and to read impedance of the antenna. Another term for "writer/reader" is "interrogator".

In accordance with embodiments disclosed herein, an LCR or an RFID sensor for sensing vapors, vapor mixtures, fluids, fluid mixtures and biological species is described. As previously described, the RFID sensor includes an RFID tag coated with a sensing material. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through an antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements.

In one embodiment a passive RFID tag with or without an IC memory chip may be employed. Advantageously, a passive RFID tag does not rely on a battery for operation. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with a writer/reader that operates at 13.56 MHz while the sensor portion of the RFID tag operates from 5 to 20 MHz.

Depositing sensing films onto passive RFID tags creates RFID chemical, biological, or physical sensors. RFID sensing is performed by measuring changes in the RFID sensor's impedance as a function of physical changes around the sensor, as described further below. Examples of physical changes include, but are not limited to, temperature, pressure, conductivity, and dielectric properties. If the frequency response of the antenna coil, after deposition of the sensing film, does not exceed the frequency range of operation of the tag, the information stored in the microchip can be identified with a conventional RFID writer/reader. Similarly, an impedance analyzer (sensor reader) can read the impedance of the antenna coil to correlate the changes in impedance to the chemical and biological species of interest and to physical, chemical, or/and biological changes of environmental parameters around the sensor.

In operation, after coating of the RFID tag with a chemically sensitive film, both the digital tag ID and the impedance of the tag antenna may be measured. The measured digital ID provides information about the identity of the tag itself, such as an object onto which this tag is attached, and the properties of the sensor (e.g. calibration curves for different conditions, manufacturing parameters, expiration date, etc.). For multi-component detection, multiple properties from the measured real and imaginary portions of the impedance of a single RFID sensor may be determined, as described further below.

In alternate embodiments, the selective sensor performance can be achieved not only by using a sensing material deposited onto the transducer, but also by depositing a protective film onto the transducer, or using the bare transducer itself.

In accordance with the embodiments described herein, in order to achieve high selectivity detection of analytes in the presence of high levels of interferences, the sensor should exhibit a number of characteristics. First, the selected transducer should include a multivariate output to independently detect the effects of different environmental parameters on the sensor. Second, the sensing material should have a preserved magnitude of response to an analyte over a wide concentration range of an interferent. The response to the relatively small analyte concentrations should not be fully suppressed by the presence of the relatively high concentrations of the interferents. Third, the response of the sensing material to interference species is allowed and may exist but should not compete with the response to the analyte and should be in a different direction of the multivariate output response of the transducer.

To achieve these characteristics, in one embodiment, the sensing material has multiple response mechanisms to fluids where these response mechanisms are related to the changes of dielectric constant, resistance, and swelling of the sensing material where these changes are not fully correlated with each other and produce different patterns upon exposure to individual vapors and their mixtures. Further, the LCR transducer can have multiple components of LCR response from the LCR circuit where these multiple components of LCR response originate from the different factors affecting the transducer circuit with the nonlimiting examples that include material resistance and capacitance, contact resistance and capacitance between the transducer and sensing material, resistance and capacitance between the transducer substrate and sensing material. Further, the LCR transducer can have multiple conditions of LCR circuit operation where an integrated circuit chip is a part of the sensor circuit.

Thus, one method for controlling the selectivity of the sensor response involves powering of the integrated circuit chip to affect the impedance spectral profile. The different impedance spectral profiles change the selectivity of sensor response upon interactions with different fluids. The IC chip or IC memory chip on the resonant antenna contains a rectifier diode and it can be powered at different power levels to influence the impedance spectral profile of the sensor. The differences in spectral profiles at different power levels are pronounced in different values of Fp, F1, F2, Fz, Zp, Z1, Z2, and calculated values of C and R. In one embodiment, the enhanced sensor selectivity is achieved through the appropriate selection of at least one power level of the IC chip or IC memory chip operation. In another embodiment, the enhanced sensor selectivity is achieved through the appropriate selection of at least two power levels of the IC chip or IC memory chip operation and analyzing the combined impedance spectral profiles of the sensor under different power levels. Powering of the sensor with at least two power levels is performed in the alternating fashion between a relatively low and relatively high power. The alternating powering of the sensor with at least two power levels is performed on the time scale which is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences.

Another method of controlling the selectivity of the sensor response involves applying different powers to the LCR or to RFID sensor to affect the dipole moment, the dielectric constant, and/or temperature of the material in proximity to the sensor. The material in proximity to the sensor refers to the sensing material deposited onto the sensor and/or the fluid under investigation. These changes in the dipole moment, the dielectric constant, and/or temperature of the material in proximity to the sensor when exposed to different power levels of LCR or RFID sensor operation originate from the interactions of the electromagnetic field with these materials. Powering of the sensor with at least two power levels is performed in the alternating fashion between a relatively low and relatively high power. The alternating powering of the sensor with at least two power levels is performed on the time scale which is at least 5 times faster than the dynamic changes in the measured environmental parameters. In all these embodiments, powering at different power levels is in the range from −50 dBm to +40 dBm and provides the ability to detect more selectively more analytes and/or to reject more selectively more interferences. Operation at a selected power or at multiple powers results in selective detection of fluids with the same dielectric constant.

Figure 2:
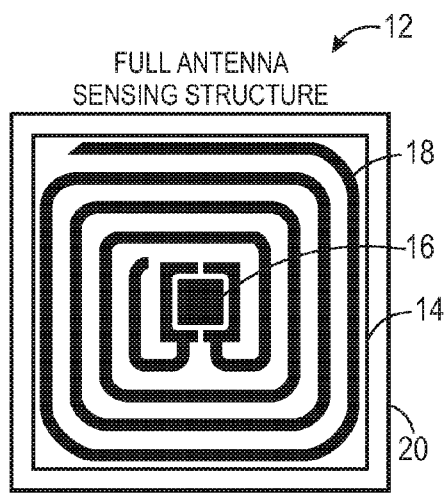
FIG. 2 illustrates an RFID sensor, in accordance with embodiments of the invention.

Turning now to the figures and referring initially to FIG. 1, a sensing system 10 is provided to illustrate the principle of selective vapor sensing utilizing an RFID sensor 12 having a sensing material 14, coated thereon. Referring briefly to FIG. 2, the sensor 12 is a resonant circuit that includes an inductor-capacitor-resistor structure (LCR) coated with the sensing material 14. The sensing material 14 is applied onto the sensing region between the electrodes, which form sensor antenna 18 that constitute the resonant circuit. As will be described further below, by applying the sensing material 14 onto the resonant circuit, the impedance response of the circuit will be altered. The sensor 12 may be a wired sensor or a wireless sensor. The sensor 12 may also include a memory chip 16 coupled to resonant antenna 18 that is coupled to a substrate 20. The memory chip 16 may include manufacturing, user, calibration and/or other data stored thereon. The memory chip 16 is an integrated circuit device and it includes RF signal modulation circuitry fabricated using a complementary metal-oxide semiconductor (CMOS) process and a non-volatile memory. The RF signal modulation circuitry components include a diode rectifier, a power supply voltage control, a modulator, a demodulator, a clock generator, and other components.

Figure 3:
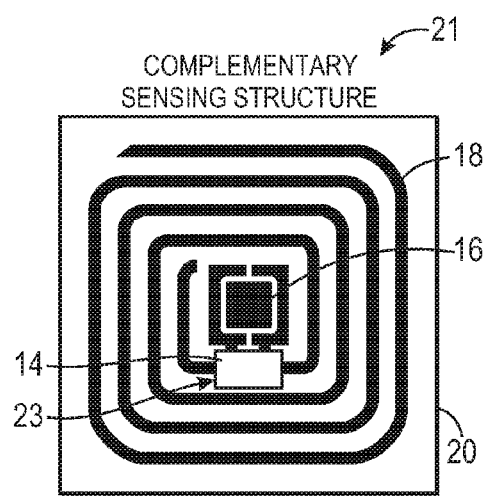
FIG. 3 illustrates an RFID sensor, in accordance with alternate embodiments of the invention.

FIG. 3 illustrates an alternative embodiment of the sensor 12, designated by reference numeral 21, wherein a complementary sensor 23 comprising a sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Nonlimiting examples of complementary sensors are interdigitated sensors, resistive sensors, and capacitive sensors. Complementary sensors are described in U.S. patent application Ser. No. 12/118,950 entitled "Methods and systems for calibration of RFID sensors", which is incorporated herein by reference.

In one embodiment, a 13.56 MHz RFID tag may be employed. During operation of the sensing system 10, the impedance Z(f) of the sensor antenna 18 and the digital sensor calibration parameters stored on the memory chip 16 may be acquired. Referring again to FIGS. 2 and 3, measurement of the resonance impedance Z(f) of the antenna 18 and the reading/writing of digital data from the memory chip 16 are performed via mutual inductance coupling between the RFID sensor antenna 18 and the pickup coil 22 of a reader 24. As illustrated, the reader 24 may include an RFID sensor impedance reader 26 and an integrated circuit memory chip reader 28. The interaction between the RFID sensor 12 and the pickup coil 22 can be described using a general mutual inductance coupling circuit model. The model includes an intrinsic impedance $Z_C$ of the pickup coil 22 and an intrinsic impedance $Z_S$ of the sensor 12. The mutual inductance coupling M and the intrinsic impedances $Z_C$ and $Z_S$ are related through the total measured impedance $Z_T$ across the terminal of the pickup coil 22, as represented by the following equation:

$$Z_T = Z_C + (\omega^2 M^2 / Z_S), \quad (1)$$

wherein $\omega$ is the radian carrier frequency and M is the mutual inductance coupling coefficient.

Sensing is performed via monitoring of the changes in the properties of the sensing material 14 as probed by the electromagnetic field generated in the antenna 18 (FIG. 2). Upon reading the RFID sensor 12 with the pickup coil 22, the electromagnetic field generated in the sensor antenna 18 extends out from the plane of the sensor 12 and is affected by the dielectric property of an ambient environment providing the opportunity for measurements of physical, chemical, and biological parameters. For measurements of highly conducting species (liquids or solids), the protecting or sensing material 14 provides a protective barrier that separates the conducting medium from the resonant antenna. For measurement in highly conducting media, the protecting or sensing material 14 prevents the RFID tag from direct contact with the liquid and loss of the sensor resonance. For measurements of low conducting media (e.g., approximately 0.5 μS/cm), the sensor can operate and perform measurements without a protecting material.

Similarly, sensing is performed via monitoring of the changes in the properties of the sensing material 14 as probed by the electromagnetic field generated in the complementary sensor 23 (FIG. 3). Upon reading the RFID sensor 21 with the pickup coil 22, the electromagnetic field generated in the complementary sensor 23 extends out from the plane of the complementary sensor 23 and is affected by the dielectric property of an ambient environment providing the opportunity for measurements of physical, chemical, and biological parameters. For measurements of highly conducting species (liquids or solids), the protecting or sensing material 14 provides a protective barrier that separates the conducting medium from the resonant antenna. For measurement in highly conducting media, the protecting or sensing material 14 prevents the RFID tag from direct contact with the liquid and loss of the sensor resonance. For measurements of low conducting media, the sensor can operate and perform measurements without a protecting material.

Figure 4:
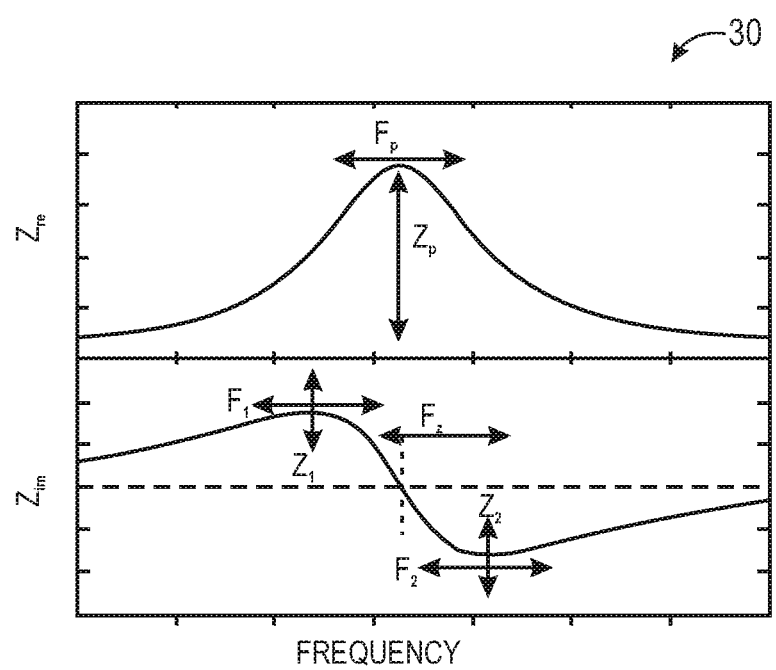
FIG. 4 illustrates measured responses of an RFID sensor, in accordance with embodiments of the invention.

FIG. 4 illustrates an example of measured responses of an exemplary RFID sensors 12 and 21, in accordance with embodiments of the invention, which includes the sensor's full impedance spectra and several individually measured spectral parameters. To selectively detect several vapors or fluids using a single RFID sensor, such as the RFID sensors 12 and 21, the real $Z_{re}(f)$ and imaginary $Z_{im}(f)$ parts of the impedance spectra $Z(f)=Zre(f)+jZ_{im}(f)$ are measured from the sensors 12 and 21 coated with a sensing material and at least four spectral parameters are calculated from the measured $Z_{re}(f)$ and $Z_{im}(f)$, as illustrated in the plot 30 of FIG. 4. Seven spectral parameters can be calculated as illustrated in the plot 30 of FIG. 4. These parameters include the frequency position Fp and magnitude Zp of $Z_{re}(f)$, the resonant F1 and anti-resonant F2 frequencies of $Z_{im}(f)$, the impedance magnitudes Z1 and Z2 at F1 and F2 frequencies, respectively, and the zero-reactance frequency FZ. Additional parameters, such as quality factor may also be calculated. From the measured parameters, resistance R, capacitance C, and other parameters of the sensors 12 and 21 can be also determined Multivariate analysis may be used to reduce the dimensionality of the impedance response, either from the measured real $Z_{re}(f)$ and imaginary $Z_{im}(f)$ parts of the impedance spectra or from the calculated parameters Fp, Zp, F1 and F2, and possibly other parameters to a single data point in multi-dimensional space for selective quantization of different vapors or fluids, as will be appreciated by those skilled in the art, and as will be described further below.

The presence of even relatively low levels of interferences (0.1-10 fold overloading levels) represents a significant limitation for individual sensors due to their insufficient selectivity. This problem can be addressed with an introduction of a concept of sensor arrays. Unfortunately, in practical situations (e.g. urban, environmental, and workplace monitoring, breath analysis, and others), sensor arrays suffer from interference effects at high ($10^2$-$10^6$ fold) overloading levels. These interference effects reduce the use of both, sensors and sensor arrays. Advantageously, embodiments described herein provide techniques to overcome these two key scientific limitations of existing sensors and sensor arrays, such as difficulty or inability of operating with high overloading from interferences and of selective measurements of multiple vapors and their mixtures using a single sensor.

The well-accepted limitations of impedance spectroscopy in practical sensors for trace analyte detection include relatively low sensitivity and prohibitively long acquisition times over the broad frequency range. Embodiments described herein enhance the ability to measure changes in properties of the sensing material by putting the material onto the electrodes of the resonant LCR sensor circuit. Similarly, the disclosed embodiments enhance the ability to measure changes in properties of the fluid in proximity to the the electrodes of the resonant LCR sensor circuit. Experimental testing examined the effects of changing dielectric constant on sensing electrodes both with and without a resonator. Compared to the conventional impedance spectroscopy, the bare resonant LCR sensor provided an at least 100-fold enhancement in the signal-to-noise (SNR) over the smallest measured range of the dielectric constant difference ($\Delta\in$) with the corresponding improvement of detection limit of dielectric constant determinations.

Performance of the LCR sensor as analyzed using multivariate analysis tools provides an advantage of improved selectivity over the processing of individual responses of individual sensors. In particular, test results indicate the relations between Fp and Zp and the relations between calculated sensor resistance R and calculated sensor capacitance C have a much less selectivity between responses to different vapors or fluids as compared to the relations between multivariable parameters such as PC1 and PC2 and others. Further, the LCR sensors demonstrate independent contact resistance and contact capacitance responses that improve the overall selectivity of the multivariable response of the LCR sensors. This selectivity improvement originates from the independent contributions of the contact resistance and contact capacitance responses to the equivalent circuit response of the sensor.

Diverse sensing materials may be advantageously utilized on the sensing region of the LCR resonant sensor because analyte-induced changes in the sensing material film affect the impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor.

Sensing films for the disclosed LCR and RFID sensors may include a variety of materials provided the environmental changes are detectable by changes in resonant LCR circuit parameters. Non-limiting examples of possible sensing film materials are a hydrogel such as poly(2-hydroxyethyl methacrylate), a sulfonated polymer such as Nafion, an adhesive polymer such as silicone adhesive, an inorganic film such as sol-gel film, a biological-containing film such as DNA, antibody, peptide or other biomolecules deposited as a film, a biological-containing film such as DNA, antibody, enzyme, peptide, polysaccharide, protein, aptamer, or other biomolecules or viruses, spores, cells, deposited as a part of a inorganic or polymeric film, a composite film, a nanocomposite film, functionalized carbon nanotube film, or film made of surface functionalized gold nanoparticles, electrospun polymeric, inorganic, and composite nanofibers, and nanoparticles that have one dielectric property and incorporated in a matrix that have another dielectric property.

Sensing materials can be selected to have different dielectric constants ranging from about 2 to about 40. Nonlimiting examples include polyisobutylene (PIB, $\in'_r=2.1$), ethyl cellulose (EC, $\in'_r=3.4$), polyepichlorihydrin (PECH, $\in'_r=7.4$), cyanopropyl methyl phenylmethyl silicone (OV-225, $\in'_r=11$), dicyanoallyl silicone (OV-275, $\in'_r=33$). The use of these materials provides the ability to tailor the relative direction of sensing response upon exposure to vapors of different dielectric constant. The different partition coefficients of vapors into these or other sensing materials further modulate the diversity and relative direction of the response.

"Composites" are materials made from two or more constituent materials with significantly different physical or chemical properties, which remain separate and distinct on a macroscopic level within the finished structure. Nonlimiting examples of composites include carbon black composites with poly(-vinylphenol), poly(styrene-co-allyl alcohol), poly(vinyl chloride-covinyl acetate), and other materials. "Nanocomposites" are materials made from two or more constituent materials with significantly different physical or chemical properties, which remain separate and distinct on a nanoscale level within the finished structure. Nonlimiting examples of nanocomposites include: carbon nanotube nanocomposites with polymers (such as poly(N-vinylpyrrolidone), polycarbonate, polystyrene, etc.); semiconducting nanocrystal quantum dot nanocomposites with polymers, metal oxide nanowires, and carbon nanotubes; metal nanoparticles or nanoclusters functionalized with carbon nanotubes.

Sensing materials exhibit analyte responses which can be described by one or more of three response mechanisms of LCR or RFID sensors such as resistance changes, dielectric constant changes and swelling changes. A composite sensing material can be constructed which incorporate multiple different individual sensing materials which each respond to analytes by predominantly different response mechanisms. Such composite sensing material produces an enhanced diversity in the multivariate response. Such composite sensing materials may be homogeneously or inhomogeneously mixed or locally patterned over specific portions of the LCR resonator.

For example, a wide range of metal oxide semiconductor materials (e.g. ZnO, $TiO_2$, $SrTiO_3$, $LaFeO_3$, etc) exhibit changes in resistance upon exposure to analyte gases, but some mixed metal oxides (e.g. $CuO$—$BaTiO_3$, $ZnO$—$WO_3$) change their permittivity/capacitance upon exposure to analyte vapors. By combining these materials either as mixtures, or by spatially separated deposition onto the same sensor, their separate contributions to the local environment surrounding the sensor are used to enhance the diversity of response mechanisms for a single analyte, thus enhancing selectivity.

As a further example, ligand-coated conducting (e.g. metal) nanoparticles are used as vapor and fluid sensing materials because of their strong changes in resistance due to localized swelling induced by analyte adsorption into the ligand shell and the subsequent change in tunneling efficiency between neighboring conducting nanoparticles and dielectric constant changes of the environment between these conducting nanoparticles. In combination with a dielectric polymer (nonlimiting examples include silicones, poly(etherurethane), polyisobutylene siloxane fluoroalcohol, etc.), conjugated polymer (polyaniline, polythiophene, poly(vinyl ferrocene), poly(fluorene)-diphenylpropane), poly(3,4-ethylenedioxythiophene) polypyrrole, bilypyrrole) or any other material (nonlimiting examples include porphyrins, metalloporphyrins, metallophthalocyanines, carbon nanotubes, semiconducting nanocrystals, metal oxide nanowires) that responds to analyte adsorption with more pronounced changes in capacitance or resistance, a sensor with a wider range of analyte responses is developed.

Further, in order to avoid potentially deleterious effects of disparate materials on each other in a composite sensing material (e.g. high dielectric constant medium suppressing conduction in a conductive filler material), this material components are chosen to locally phase separate due to hydrophilic/hydrophobic interactions or mutual immiscibility, allowing the different mechanisms active in each component to be sensed by the sensor. In another embodiment, a composite sensing material can be formed as sectors of individual materials deposited adjacent to each other onto a single sensor. In another embodiment, a composite sensing material can be formed as layers of individual materials deposited on top of each other onto a single sensor.

In certain embodiments, sensing materials may be porphyrins, metalloporphyrins, metallophthalocyanines, and related macrocycles. In these materials, gas sensing is accomplished either by π-stacking of the gas into organized layers of the flat macrocycles or by gas coordination to the metal center without the cavity inclusion. Metalloporphyrins provide several mechanisms of gas response including hydrogen bonding, polarization, polarity interactions, metal center coordination interactions and molecular arrangements. Molecules of porphyrins, metalloporphyrins, metallophthalocyanines, and related macrocycles can be also assembled into nanostructures.

Further types of materials include aligned nanostructures where alignment is performed by various known methods (dielectrophoretic alignment, alignment during material polymerization, alignment due to spatial confinement, alignment during slow solvent evaporation, and others), self-assembled structures such as colloidal crystal structures of the same size of particles, multilayers of colloidal crystal films where different layers have different size of assembled particles, nanoparticle assemblies where the particles have core-shell structure with the particle core of one dielectric property and particle shell of another dielectric property, bio-inspired materials, zero-dimensional nanomaterials, one-dimensional nanomaterials, two-dimensional nanomaterials, and three-dimensional nanomaterials.

Self-assembled structures include colloidal crystal structures of the same size of particles, multilayers of colloidal crystal films where different layers have different sizes of assembled particles, nanoparticle assemblies where the particles have core-shell structure with the particle core of one dielectric property and particle shell of another dielectric property. Nonlimiting examples of materials of self-assembled colloidal crystal structures include polystyrene, polymethylmethacrylate, polyvinyltoluene, styrene/butadiene copolymers, styrene/vinyltoluene copolymers, and silica. The typical diameters of these colloidal particles depend on the type of material and may range from 50 nanometers to 25 micrometers. Nonlimiting examples of colloidal crystal structures with multiple layers include at least one layer of particles of one size assembled as a colloidal array onto the sensor substrate and at least one layer of particles of another size assembled as a colloidal array on top of the previous layer. Nonlimiting examples of bio-inspired materials include super hydrophobic or super-hydrophilic materials.

Nonlimiting examples of zero-dimensional nanomaterials include metal nanoparticles, dielectric nanoparticles, core-shell nanoparticles, and semiconducting nanocrystals. Nonlimiting examples of one-dimensional nanomaterials include nanotubes, nanowires, nanorods, and nanofibers. Nonlimiting examples of two-dimensional nanomaterials include graphene. Nonlimiting examples of three-dimensional nanomaterials include self assembled films of several layers of colloidal spheres.

Nonlimiting examples of nanoparticles that have core-shell structure with the particle core of one dielectric property and particle shell of another dielectric property include: metal (gold, silver, their alloy, etc.) core nanoparticles and organic shell layers (dodecanethiol, decanethiol, 1-butanethiol, 2-ethylhexanethiol, hexanethiol, tert-dodecanethiol, 4-methoxy-toluenethiol, 2-mercaptobenzoxazole, 11-mercapto-1-undecanol, 6-hydroxyhexanethiol); polymeric core (polystyrene, polymethylmethacrylate) and inorganic shell (silica); isolating core (polystyrene, polymethylmethacrylate, silica) and semiconducting shell (carbon nanotubes, $TiO_2$, $ZnO$, $SnO_2$, $WO_3$), and carbon nanotube core that is decorated with metal nanoparticles. The nanoparticles of metal (gold, silver, their alloy, etc.) core nanoparticles and organic shell layers can be further modified with organic and polymeric molecules. Nonlimiting example of organic molecules include porphyrins, metalloporphyrins, metallophthalocyanines, and macrocycles, cavitands, surpamolecular compounds. Nonlimiting example of polymeric molecules include polymeric molecules with different dielectric constants ranging from 2 to 40. Nonlimiting examples include polyisobutylene (PIB, $\in'_r=2.1$), ethyl cellulose (EC, $\in'_r=3.4$), polyepichlorihydrin (PECH, $\in'_r=7.4$), cyanopropyl methyl phenylmethyl silicone (OV-225, $\in'_r=11$), dicyanoallyl silicone (OV-275, $\in'_r=33$). A nonlimiting example of fabrication of these sensing materials involves (1) preparation of metal core nanoparticles with an organic shell in a solvent, (2) mixing this composition with another composition of polymeric or organic molecules in a solvent, and (3) depositing a sensing film on an LCR or RFID transducer from this combined mixture. The use of these materials in combination with metal core nanoparticles provides the ability to tailor the relative direction of sensing response upon exposure to vapors of different dielectric constant. The different partition coefficients of vapors into these or other sensing materials further modulate the diversity and relative direction of the response.

Other sensing materials include semiconducting metal oxides, zeolites, cavitands, ionic liquids, liquid crystals, crown ethers, enzymes, polysilsesquioxanes, metal-organic frameworks (MOFs).

Other sensing materials include synthetic dielectric and conducting polymers with different polymer side group functionalities, and different polymer formulations; biomolecules for gas-phase sensing; cavitands with dominating intracavity complexation and a totally suppressed non specific extracavity adsorption of vapors provided by cavitand deposition; porphyrins and related molecules as individual molecules and as assembled into polymers and nanostructures.

To further improve selectivity of response, overcoating of sensing films with auxiliary membrane filter films may be performed. Nonlimiting examples of these filter films include zeolite, metal-organic framework, and cavitand filters.

These diverse sensing materials shown as nonlimiting examples are provided on the sensing region of the LCR or RFID resonant sensor because analyte-induced changes in the sensing material film affect the complex impedance of the antenna LCR circuit through the changes in material resistance and capacitance, contact resistance and capacitance between the transducer and sensing material, resistance and capacitance between the transducer substrate and sensing material. Such changes provide diversity in response of an individual RFID sensor and provide the opportunity to replace a whole array of conventional sensors with a single LCR or RFID sensor, as illustrated further below, with regard to EXPERIMENTAL DATA.

Experimental Data

Resonant antenna structures, such as those described above, were used for demonstration of the disclosed techniques. Various sensing materials were applied onto the resonant antennas by conventional draw-coating, drop coating, and spraying processes. Measurements of the impedance of the RFID and LCR sensors were performed for example with a network analyzer (Model E5062A, Agilent Technologies, Inc. Santa Clara, Calif.) under computer control using LabVIEW. The network analyzer was used to scan the frequencies over the range of interest (i.e., the resonant frequency range of the LCR circuit) and to collect the impedance response from the RFID and LCR sensors.

For gas sensing, different concentrations of vapors were generated using an in-house built computer-controlled vapor-generation system. Collected impedance data was analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

EXAMPLE 1

Selective Detection of Six Vapors with a Single Sensor

Figure 5:
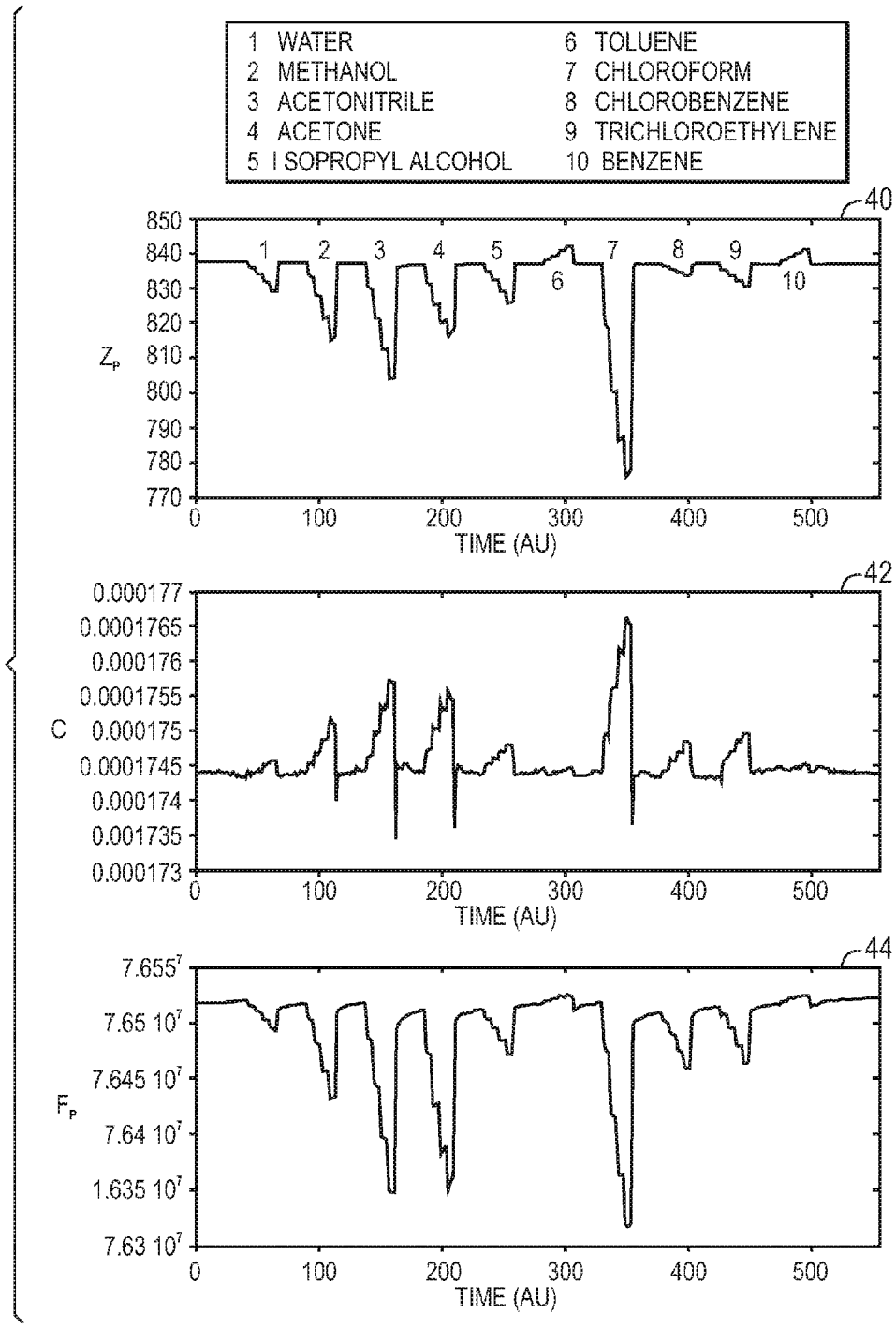
FIGS. 5 and 6 illustrate test data demonstrating an RFID sensor capable of detecting six different vapors, in accordance with embodiments of the invention.
Figure 6:
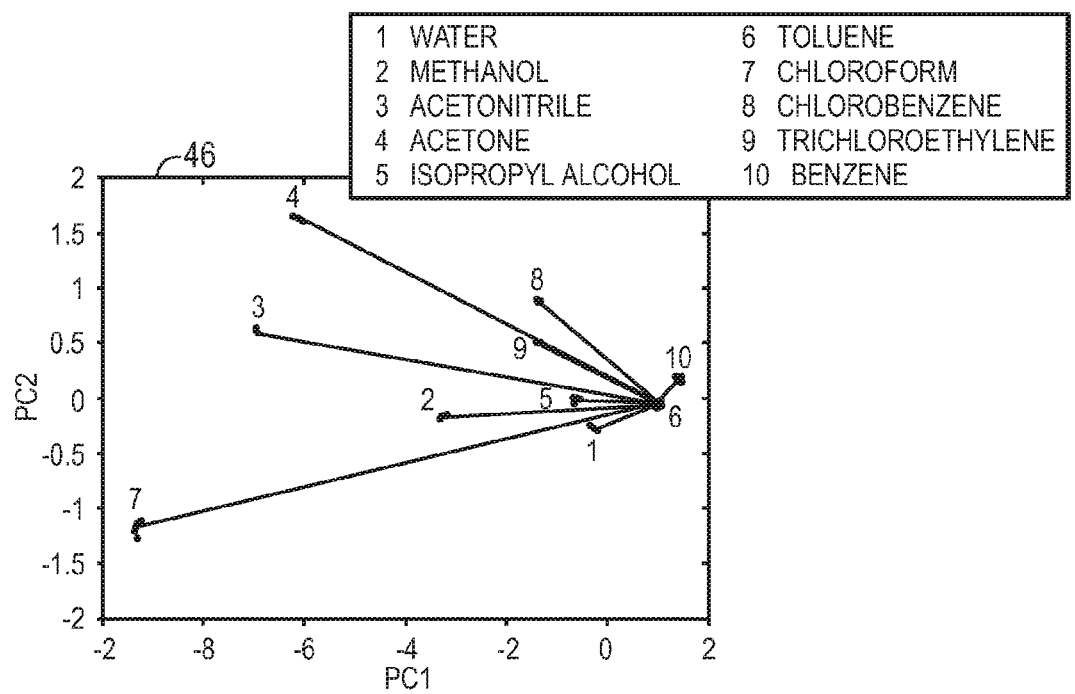

As illustrated in FIGS. 5 and 6, test results were obtained to demonstrate the selective detection of six different vapors, using a single sensor, such as the sensor 12 described above.

As illustrated in FIG. 5, the sensor was exposed to the following 10 vapors over a period of time:

| | | |
|---|---|---|
| 1 | water | |
| 2 | methanol | |
| 3 | acetonitrile | |
| 4 | acetone | |
| 5 | isopropyl alcohol | |
| 6 | toluene | |
| 7 | chloroform | |
| 8 | chlorobenzene | |
| 9 | trichloroethylene | |
| 10 | benzene | |

The sensing material used to coat the RFID tag was carefully chosen and provided the ability to selectively detect at least six of the listed vapors. In the present experiment, the chosen sensing material was poly(etherurethane) (PEUT) dissolved in a nonpolar solvent such as dichloromethane. During the experiment, the RFID sensor was incrementally exposed to 10 vapors over a period of time. The test was conducted in steps, where the concentration of each respective vapor was increased with each step. By monitoring changes in certain properties and examining various responses over time and at increasing concentration levels, the data demonstrated the ability to distinguish six of the 10 vapors tested in the above-described experiment.

For instance, the frequency position Fp and magnitude Zp of the real part of the total resistance $Z_{re}(f)$, as well as the capacitance C, are illustrated in FIG. 5, as response plots 44, 40 and 42, respectively. The tests for each vapor were conducted and plotted over 4 increments of increasing concentration, as clearly indicated by the stepped nature of the response for each vapor. For example, referring to the plot of the magnitude Zp, the magnitude Zp for each vapor (1-10) exhibits four steps, correlative to the increases in concentration of each vapor over time. From examining this plot alone, certain of the vapors can clearly be distinguished from one another. By way of example, the magnitude Zp response for chloroform (7) is very strong, and it notably discernable from each of the other responses. Accordingly, the exemplary RFID sensor is able to selectively detect chloroform (7). In contrast, when viewing the magnitude Zp response of methanol (2), it appears very similar to the magnitude Zp of acetone (4). Based solely on the magnitude Zp response, the exemplary RFID sensor may not be suitable for detecting and distinguishing between these two vapors.

However, as previously described, a number of other responses (e.g. the frequency position Fp and the capacitance C) may also be analyzed and may provide further information that may be manipulated and analyzed in order to provide a way to distinguish vapors, wherein one particular response may not be sufficient. Referring to the test data for frequency position Fp response plot 44, the frequency position Fp of methanol (2) is distinguishable from the frequency position Fp of acetone (4). Accordingly, the exemplary RFID sensor may be sufficient for distinguishing such vapors, when other responses, such as the frequency position Fp (as opposed to the magnitude Zp response alone), are analyzed.

One convenient way of analyzing various responses of the sensor is to use principal components analysis (PCA) to produce a multivariate signature. As will be appreciated, PCA analysis is a mathematical process, known to those skilled in the art, that is used to reduce multidimensional data sets to lower dimensions for analysis. For instance, the various responses for each vapor at a given concentration may be reduced to a single data point, and from this, a single response for each vapor which may be represented as a vector, may be discerned, as illustrated in FIG. 6. FIG. 6 represents a PCA plot 46 of the various responses of the 10 vapors described with reference to FIG. 5. As will be appreciated, PC1 represents the response with the most variation, while PC2 represents the response with the next most variation. As illustrated, the vectors for acetone (4) and trichloroethylene (9) may be difficult to distinguish from one another. Similarly, the vectors for toluene (6) and benzene (10) may be difficult to distinguish from one another. However, the remaining six vapors are clearly distinguishable from one another. Accordingly, the instant test data provides support for a sensor capable of discerning between at least six vapors, here water (1), methanol (2), acetonitrile (3), isopropyl alcohol (5), chloroform (7), and chlorobenzene (8).

In addition, vapor mixtures may also be discernable from the PCA plot. For instance, one may be able to extrapolate a vector plot of a mixture of acetonitrile (3) and chloroform (7). Such additional extrapolated data may also be used to selectively detect mixtures of selected vapors. Further, by varying the selected sensing material, even greater numbers of selective vapor detection has been demonstrated, utilizing a single RFID sensor.

EXAMPLE 2

Selective Detection of Eight Vapors with a Single Sensor

Figure 7:
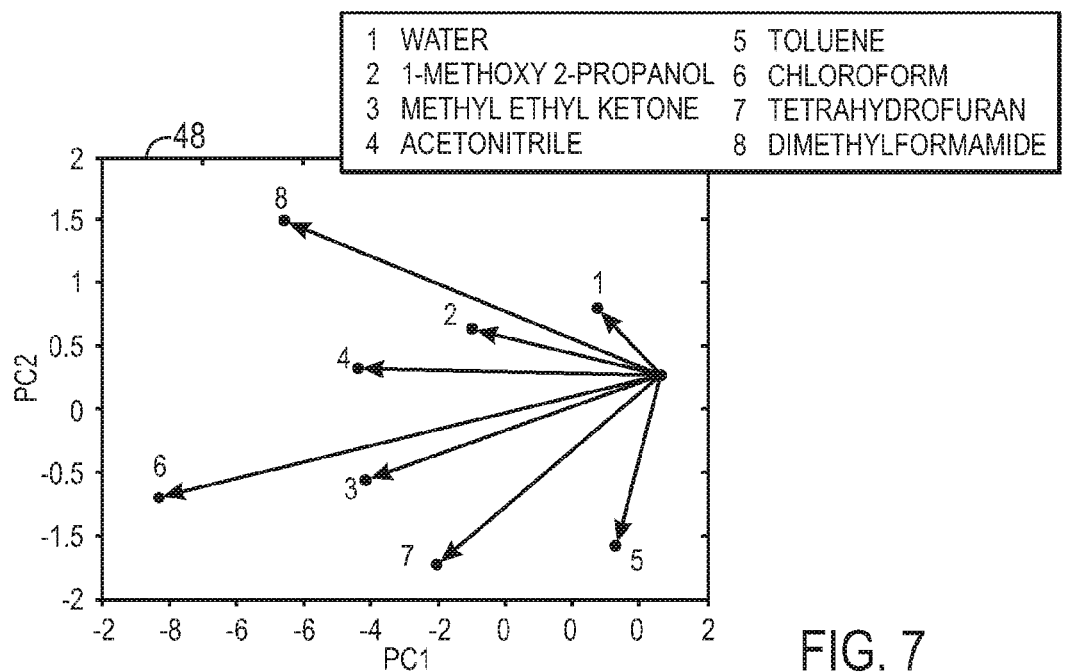
FIG. 7 illustrates test data demonstrating an RFID sensor capable of detecting eight different vapors, in accordance with embodiments of the invention.

As illustrated in FIG. 7, test results were obtained to demonstrate the selective detection of eight different vapors, using a single sensor, such as the sensor 12 described above. The sensing material used to coat the RFID tag was carefully chosen and provided the ability to selectively detect the listed vapors. In the present experiment, the chosen sensing material was PEUT dissolved in a nonpolar solvent such as dichloromethane. As previously described, the tests were conducted with incremental increases in concentration. As illustrated in the plot 48 of FIG. 7, the sensor coated with PEUT was able to discriminate the following 8 vapors:

| | | |
|---|---|---|
| 1 | water | |
| 2 | 1-methoxy 2-propanol | |
| 3 | methyl ethyl ketone | |
| 4 | acetonitrile | |
| 5 | toluene | |
| 6 | chloroform | |
| 7 | tetrahydrofuran | |
| 8 | dimethylformamide | |

EXAMPLE 3

Selective Detection of Binary and Ternary Mixtures with a Single Sensor

Figure 8:
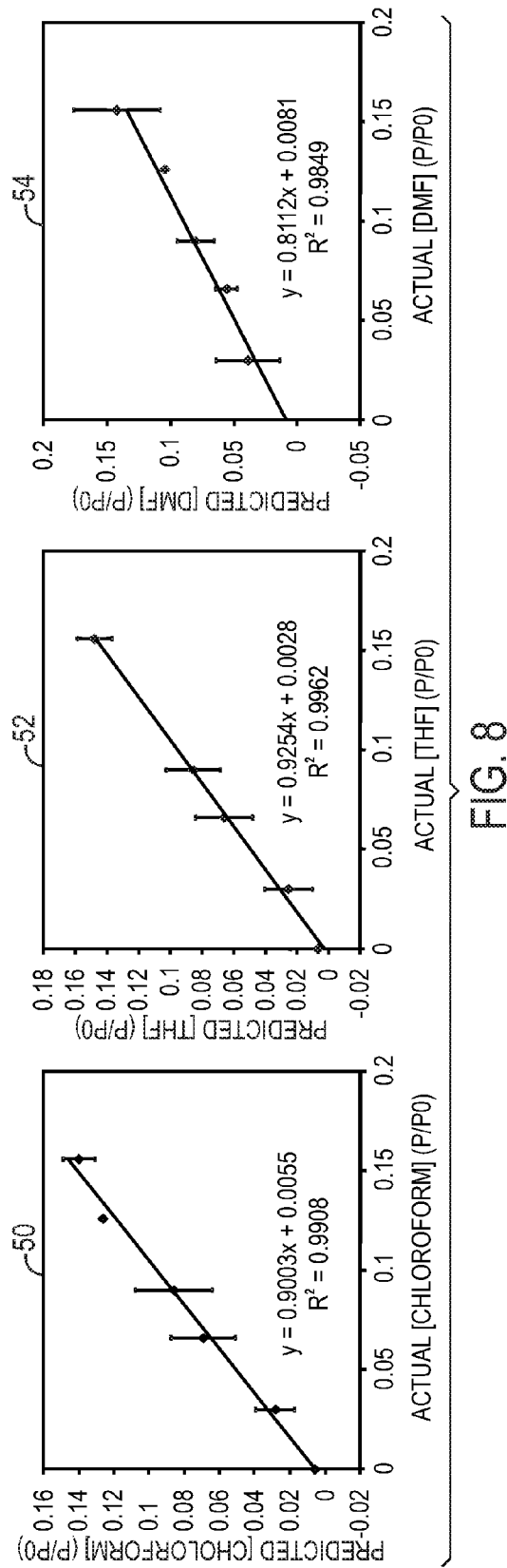
FIG. 8 illustrates test data demonstrating a single sensor capable of determining concentrations of individual vapors in their binary and ternary mixtures, in accordance with embodiments of the invention.

Vapors chloroform, tetrahydrofuran (THF), and dimethylformamide (DMF) were further selected for measurements of binary and ternary mixtures with a single sensor, as described in EXAMPLE 1. Using a single developed sensor, detection of individual vapors in their binary and ternary mixtures was demonstrated, as illustrated in FIG. 8. Correlation plots 50, 52 and 54, corresponding to chloroform, THF and DMF, respectively, between actual and predicted concentrations of the individual vapors in their mixtures, had excellent correlation coefficients. Vapors concentrations were from 0 to 0.15 P/Po where P is the partial pressure and Po is the saturated vapor pressure. These results demonstrated a unique ability of developed individual sensors to quantify 2-3 vapors in their mixtures. This discrimination has become possible because the sensor's multivariable response was modeled using the first, second, and third principal components (PCs) of the built PCA model.

EXAMPLE 4

Selective Detection of Nine Vapors with a Single Sensor in the Presence of Variable Relative Humidity In this EXAMPLE, an RFID sensor (as described in EXAMPLE 1) coated with PEUT was also tested and a PCA evaluation demonstrated an RFID sensor capable of discriminating between up to nine vapors in the presence of variable relative humidity. Specifically, ethanol, 1-methoxy 2-propanol, methyl ethyl ketone, acetonitrile, toluene, choloroform, tetrahydrofuran (THF) dimethylformanmide (DMF) and acetone were selectively detected. In certain embodiments, the PCA analysis data may also be plotted in three dimensions, thereby providing an even greater ability to discriminate among various vapors.

EXAMPLE 5

Selective Detection of Individual Nine Alcohols with a Single Sensor

Figure 9:
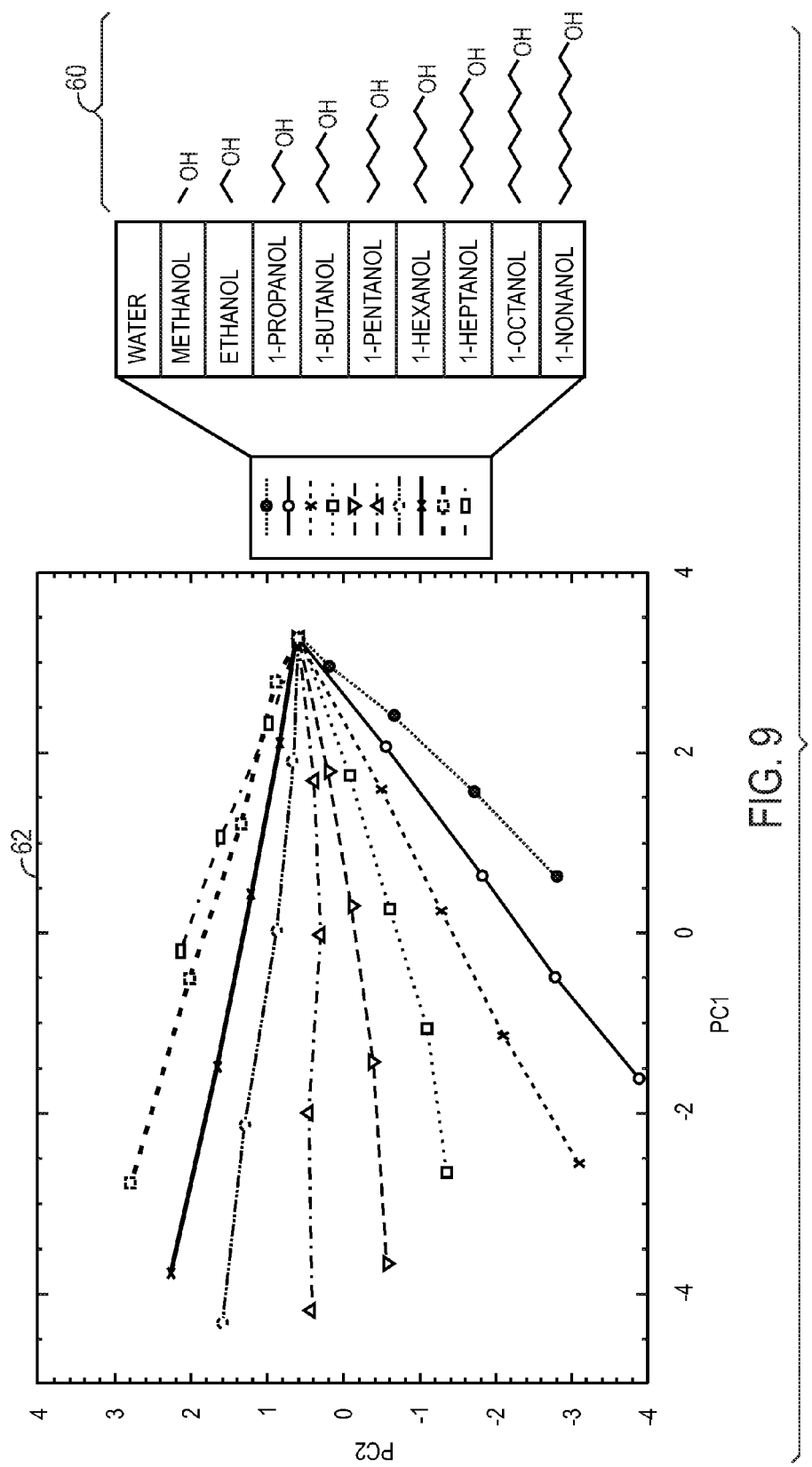
FIG. 9 illustrates test data demonstrating a single sensor capable of discriminating between water vapor and nine individual alcohol vapors from their homologous series, in accordance with embodiments of the invention.

With recognition of eight and nine diverse vapors demonstrated implementing sensors disclosed herein (EXAMPLEs 2 and 4, respectively), further testing was conducted to demonstrate selective detecting of individual, closely related vapors, such as alcohols from their homologous series and water vapor as an interferent. The tested sensing film made of octanethiol-capped Au nanoparticles was applied onto a sensor by drop casting. The structures of alcohols 60 are illustrated in FIG. 9. Results of selectivity evaluation of the sensor are also illustrated where a single sensor discriminates between water vapor and individual nine alcohol vapors from their homologous series, as shown by the PCA scores plot 62. Measurements were performed with concentrations of all vapors at 0, 0.089, 0.178, 0.267, and 0.356 $P/P_o$. No previous individual sensor has been reported to achieve this level of vapor discrimination, while this discrimination was achieved here with a single sensor.

EXAMPLE 6

Rejection of 300,000-1,900,000-Fold Overloading from Water Vapor

Figure 10:
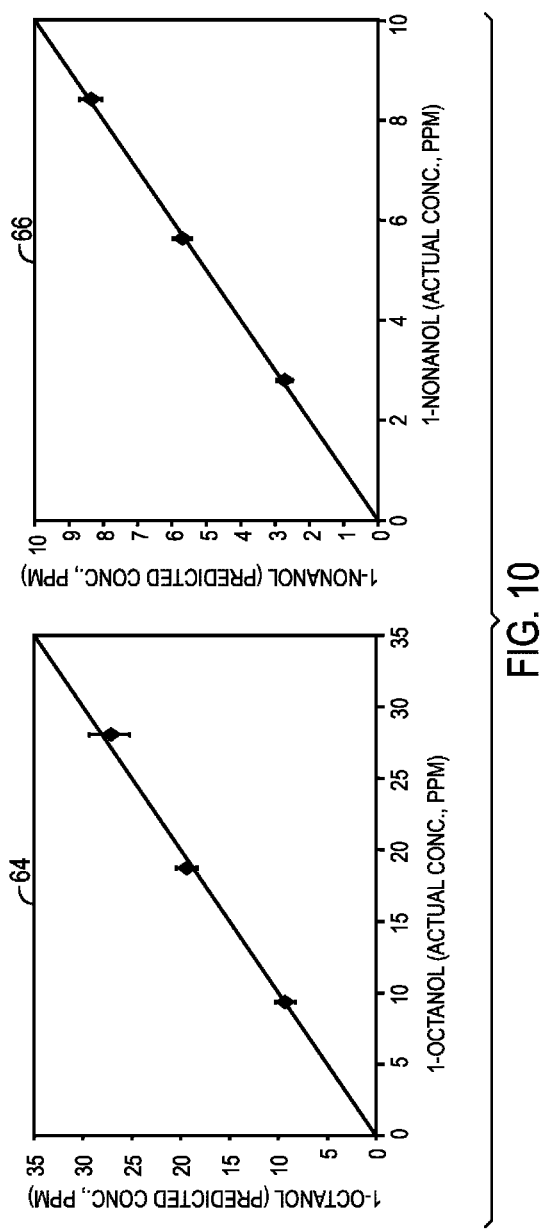
FIG. 10 illustrates comparative plots between the actual and predicted concentrations of 1-octanol and 1-nonanol, in accordance with embodiments of the invention.

The sensor described in EXAMPLE 5 was further tested for rejection of water vapor interference from measured multivariable sensor response of two polar model analytes (1-octanol and 1-nonanol). The sensor response to analyte vapors in mixtures with water vapor was corrected using multivariate analysis. FIG. 10 illustrates correlation plots 64 and 66 between the actual and predicted concentrations of 1-octanol (plot 64) and 1-nonanol (plot 66). Predicted concentrations of these vapors in the presence of different levels of humidity (ranging from 0 to 16,842 ppm) were calculated using multivariate analysis. The ratio of water vapor concentration to the detection limit concentration of the analyte in this mixture provided values of rejected water vapor overloading. The Tables of FIG. 11 summarize these findings for 1-octanol (Table 68) and 1-nonanol (Table 70). This data shows that a single sensor rejected up to 1,900,000-fold overloading from water vapor when measuring analyte vapors concentrations down to ppb levels.

EXAMPLE 7

Highly Selective Multivariate Vapor Sensing

Figure 12:
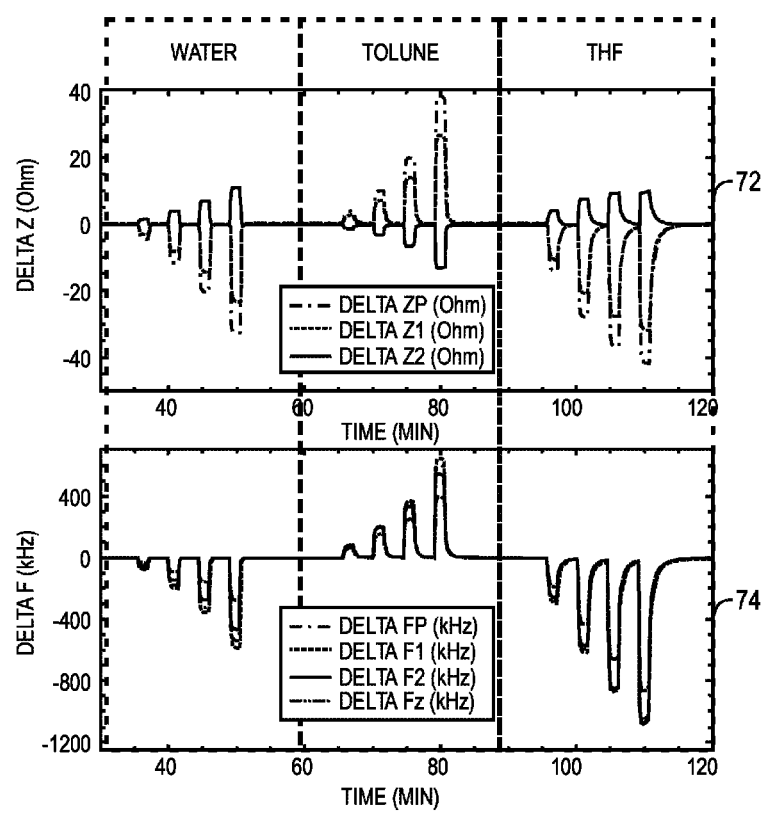
FIGS. 12-14 illustrate test data demonstrating a single sensor capable of highly selective multivariate vapor sensing, in accordance with embodiments of the invention.
Figure 13:
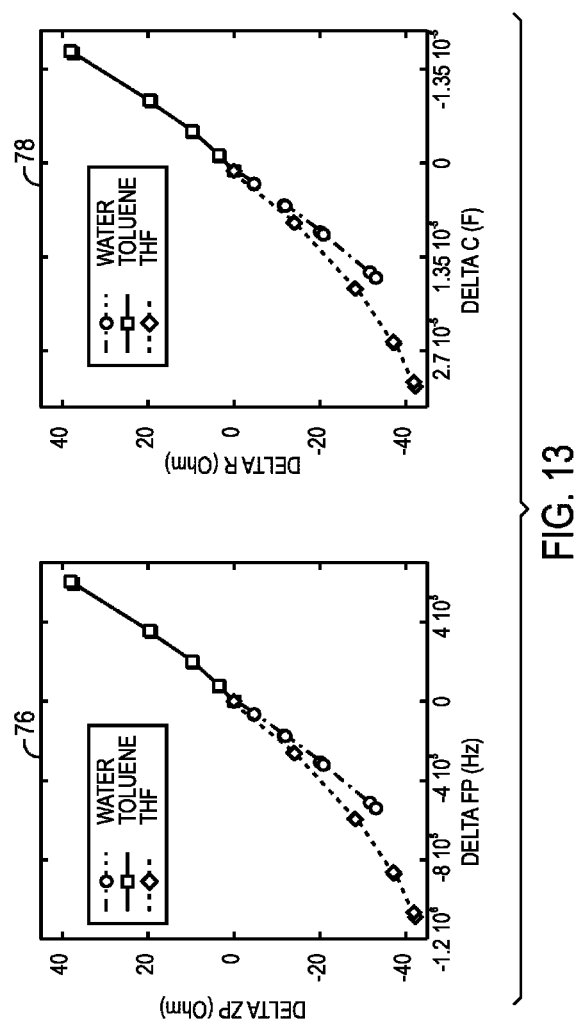
Figure 14:
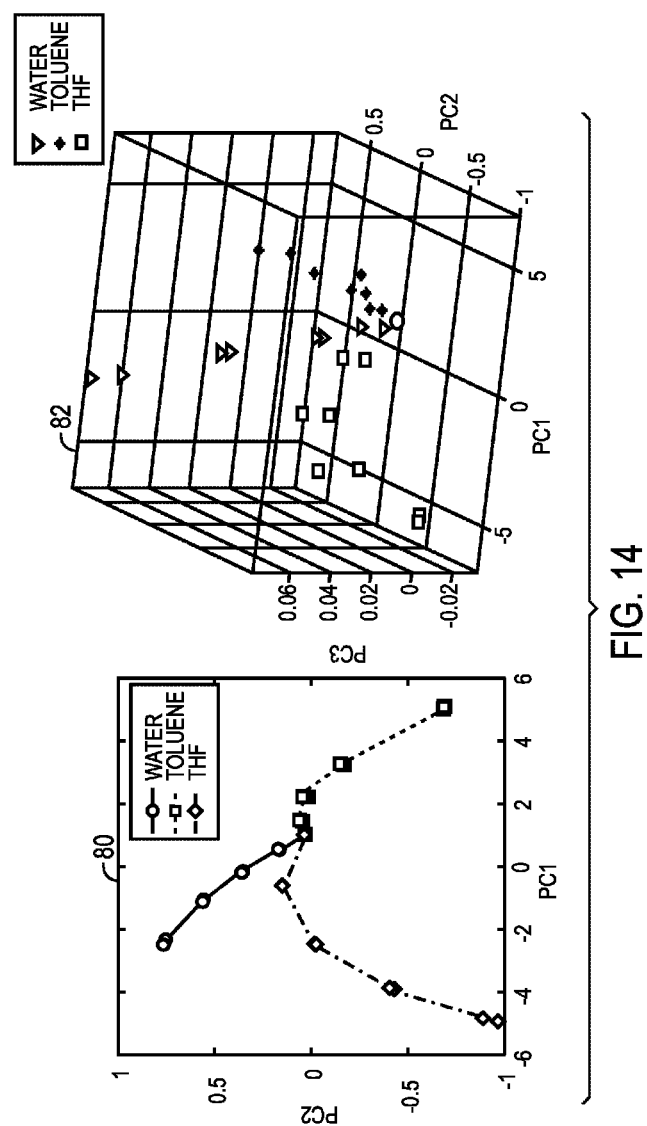

In another experiment, the sensing material used to coat the sensor was PEUT dissolved in a nonpolar solvent such as dichloromethane. During the experiment, the sensor was incrementally exposed to three vapors, water, toluene, and THF, over a period of time. Concentrations of each vapor were 0.18, 0.36, 0.53, and 0.71 P/Po. Dielectric constants of these analytes were 79 (water), 2.4 (toluene), and 7.5 (THF). As demonstrated and illustrated in FIGS. 12-14, a single passive sensor with multivariable response was able to easily discriminate between these three vapors. Specifically, the individual Fp, F1, F2, Fz, Zp, Z1 and Z2 responses, illustrated in plots 72 and 74 of FIG. 12, were analyzed using PCA tools. The relations between Fp and Zp are illustrated in plot 76 of FIG. 13, and the relations between calculated sensor resistance R and calculated sensor capacitance C are illustrated in plot 78. The plots 76 and 78 of FIG. 13 demonstrated a poor selectivity between water and THF vapors, as indicated by the closely positioned curves of water and THF responses. This poor selectivity between water and THF was because the dielectric constant of the polyetherurethane sensing film ($\in'_r$=4.8) is lower than water or THF but is higher than toluene. In contrast, the relationship between PC1 and PC2, illustrated in PCA scores plot 80 of FIG. 14, and the relationship between PC1, PC2, and PC3, illustrated in PCA scores plot 82 of FIG. 14, show a significant improvement in selectivity of sensor when data is analyzed using multivariate analysis tools. The responses for all three vapors are roughly pointing into three different directions in the 2D plot 80. Importantly, the responses PC1, PC2, and PC3 of plot 82 are in a 3D directional space demonstrating that the sensor performs as a multivariable device with three dimensions of response. Other sensors, for example, individual resistance and capacitance sensors produce only a single response per sensor. Even a combination of individual resistance and capacitance sensors produces only two responses per this combination, one response per sensor. Thus, a single multivariable response wireless sensor, in accordance with embodiments of the invention, reliably discriminated between these three example vapors using a "classic" polyetherurethane polymer.

EXAMPLE 8

Figure 15:
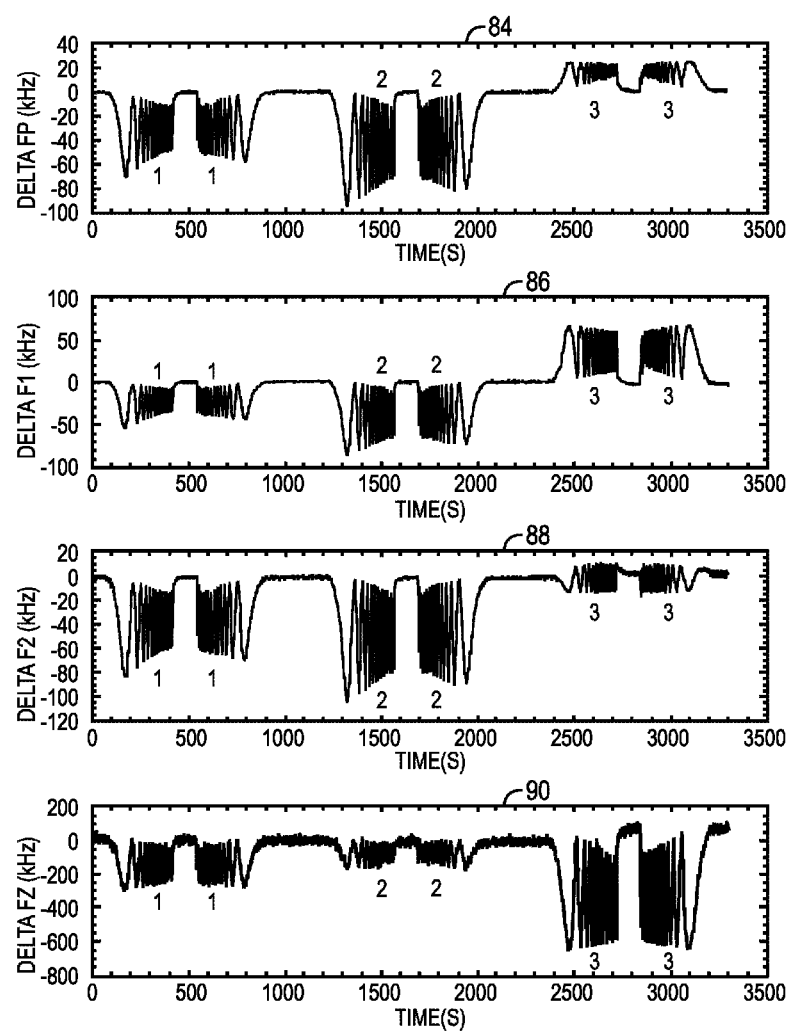
FIGS. 15-18 illustrate test data demonstrating independent contact resistance and contact capacitance responses, in accordance with embodiments of the invention.
Figure 16:
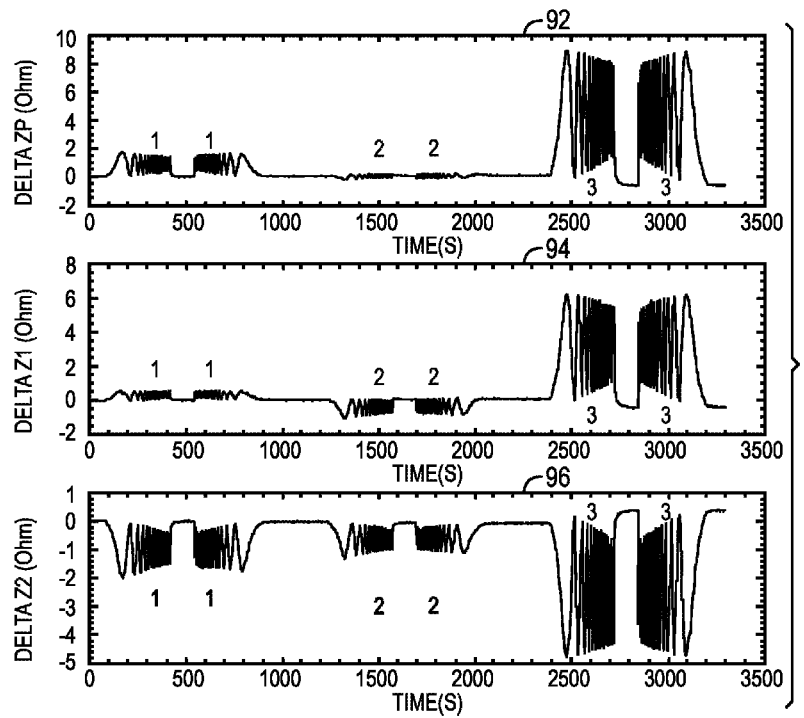

Demonstration of Independent Contact Resistance and Contact Capacitance Responses In another experiment, the sensing material used to coat the sensor was octanethiol-capped Au nanoparticles (Sigma Aldrich #6604426) mixed with zinc 1,4,8,11,15,18,22,25-octabutoxy-29H,31H-phthalocyanine (Sigma Aldrich #383813) applied onto a sensor by drop casting. During the experiment, the sensor was exposed to three vapors: acetone (vapor 1), acetonitrile (vapor 2), and toluene (vapor 3). Exposures were performed in a dynamic fashion where a vapor concentration was modulated with a sinusoidal function where its period was first reducing during the experiment and then increasing during the experiment. FIG. 15 illustrates Fp, F1, F2, and Fz dynamic responses to the three vapors, as indicated by plots 84, 86, 88 and 90, respectively. FIG. 16 illustrates Zp, Z1, and Z2 dynamic responses to the three vapors, as indicated by plots 92, 94 and 96, respectively.

This experiment was performed to explore if contributions to the vapor responses arise from the same or from different portions of the transducer circuit. If the contributions to the vapor responses arise from the same portion of the transducer circuit, then dynamic responses related to frequency shifts Fp, F1, F2, and Fz should perfectly track each other and dynamic responses related to impedance change Zp, Z1, and Z2 should also perfectly track each other. However, if the contributions to the vapor responses are arising from different portions of the transducer circuit, then dynamic responses related to Fp, F1, F2, and Fz frequency shifts and dynamic responses related to impedance change Zp, Z1, and Z2 could be different. Furthermore, these differences can be present or absent depending on the nature of vapor because of the different types of interactions of different vapors with the sensing material and the material of the electrodes of the transducer.

The modulation of vapor concentration with a variable period provides the ability to evaluate the dynamics of the response to the vapor and the recovery from the vapor exposure. If the response of the sensing material to the vapor is faster than the smallest modulation period of the vapor concentration, then the amplitude of the sensor response will be unchanged with an increased speed of vapor concentration change. However, if the response of the sensing material to the vapor is slower than a predetermined modulation period of the vapor concentration, then the amplitude of the sensor response will start decreasing with an increased speed of vapor concentration change.

Similarly, if the recovery of the sensing material upon vapor exposure is faster than the smallest modulation period of the vapor concentration, then the amplitude of the sensor recovery will be unchanged with an increased speed of vapor concentration change. However, if the recovery of the sensing material upon vapor exposure is slower than the smallest modulation period of the vapor concentration, then the amplitude of the sensor recovery will start decreasing with an increased speed of vapor concentration change.

Thus, differences in the modulation of the amplitude of the sensor response and recovery should signify the existence of the contributions to the transducer performance that are arising from the different portions of the transducer circuit. These different portions of the transducer circuit can produce an additional diversity in sensor response and can provide the ability of the individual sensor to detect multiple vapors with high selectivity. This ability of the resonant transducer is completely different from a simple combination of individual resistance and capacitance sensors that produce only two responses per combination, one response per sensor.

Figure 17:
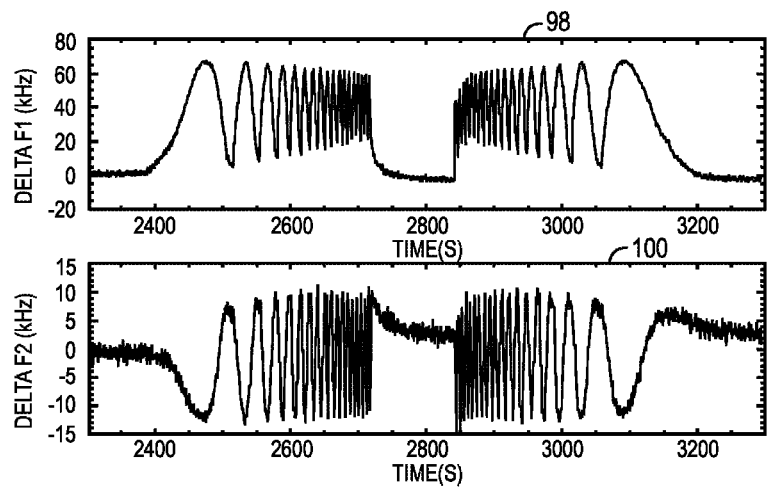
Figure 18:
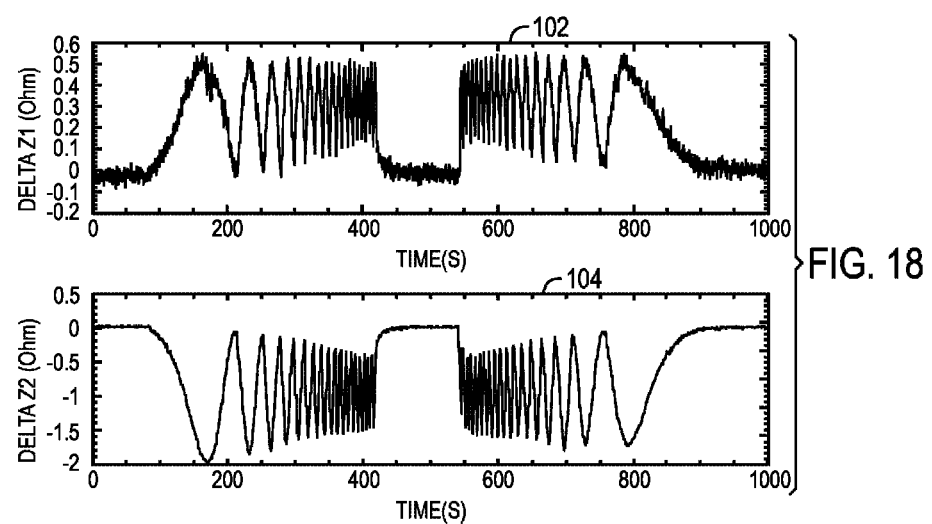

Referring to FIGS. 15-18, FIG. 15 illustrates Fp, F1, F2, and Fz dynamic responses to three vapors, and FIG. 16 illustrates Zp, Z1, and Z2 dynamic responses to three vapors such as acetone (vapor 1), acetonitrile (vapor 2), and toluene (vapor 3). The response and recovery amplitudes of vapors 1, 2, and 3 show diverse profiles. These diverse profiles are illustrated again in plots 98 and 100 of FIG. 17 for dynamic responses F1 and F2 to vapor 3 and in plots 102 and 104 for FIG. 18 for dynamic responses Z1 and Z2 to vapor 1. FIG. 17 demonstrates that vapor 3 affects different capacitance components of the transducer circuit (related to frequency changes in the LCR circuit) as evidenced by the differences in dynamic response and recovery profiles to vapor 3. FIG. 18 demonstrates that vapor 1 affects different resistance components of the transducer circuit (related to resistance changes in an LCR circuit) as evidenced by the differences in dynamic response and recovery profiles to vapor 1.

EXAMPLE 9

Highly Sensitive Multivariate Vapor Sensing

While impedance spectroscopy is a classic technique to characterize fundamental materials properties, its well-accepted limitations in practical sensors for trace analyte detection include relatively low sensitivity and prohibitively long acquisition times over the broad frequency range. Thus, in order to enhance the ability to measure changes in properties of the sensing material, the sensing material was deposited onto the electrodes of the resonant LCR sensor circuit. Similarly, this placement of the electrodes enhanced the ability to measure changes in properties of the fluid in proximity to the electrodes of the resonant LCR sensor circuit.

Figure 19:
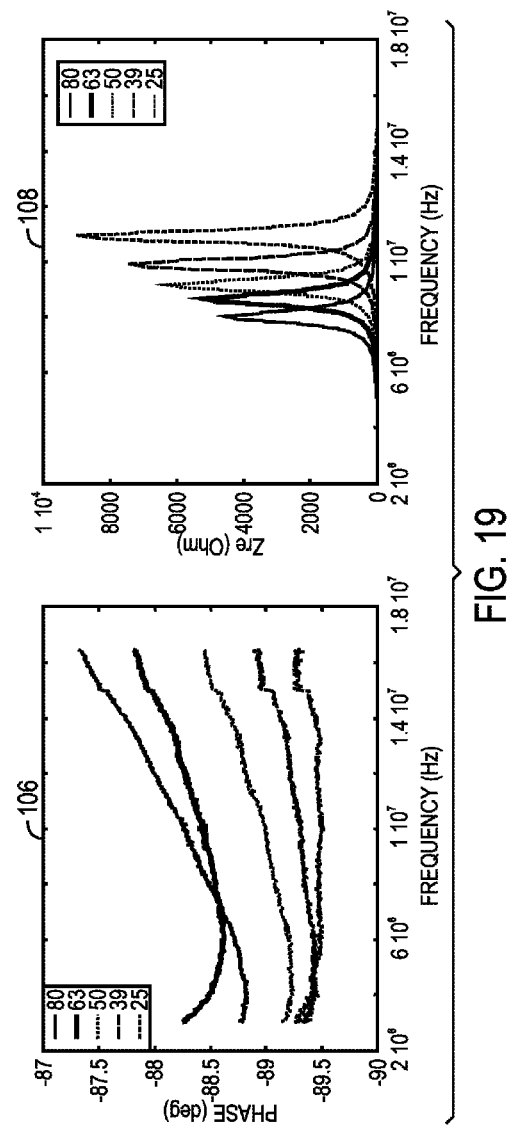
FIGS. 19-20 illustrates a comparison of conventional impedance spectroscopy and resonant sensing of embodiments having different dielectric constants.

In further experiments, effects of changing dielectric constant on sensing electrodes both with and without a resonator were tested. For example, fluids of five different dielectric constants (mixtures of water and ethanol at different ratios) were flowed into the cell and the impedance response of the sensor was monitored. The sensing ability of resonant sensors was compared with the sensing ability of resonant LCR sensors. In these comparisons, the signal-to-noise (SNR) and detection limit (DL) from two measurement configurations were determined FIG. 19 illustrates results of validation experiments with solutions of $\varepsilon=25\text{-}80$ dielectric constants where results of phase shift measurements of an impedance spectrum and the peak shift of the resonance of the sensor were compared. Specifically, a comparison of conventional impedance spectroscopy and resonant sensing using solutions of different dielectric constants are illustrated in plots 106 and 108. Plot 106 illustrates the sensor response (phase shift) measured using conventional impedance spectroscopy. Plot 108 illustrates the sensor response (frequency shift) measured using a resonance sensor structure. Five different dielectric constants c ranging from 25 to 80 were produced using solutions with different water/ethanol ratios, as illustrated in plots 106 and 108.

Figure 20:
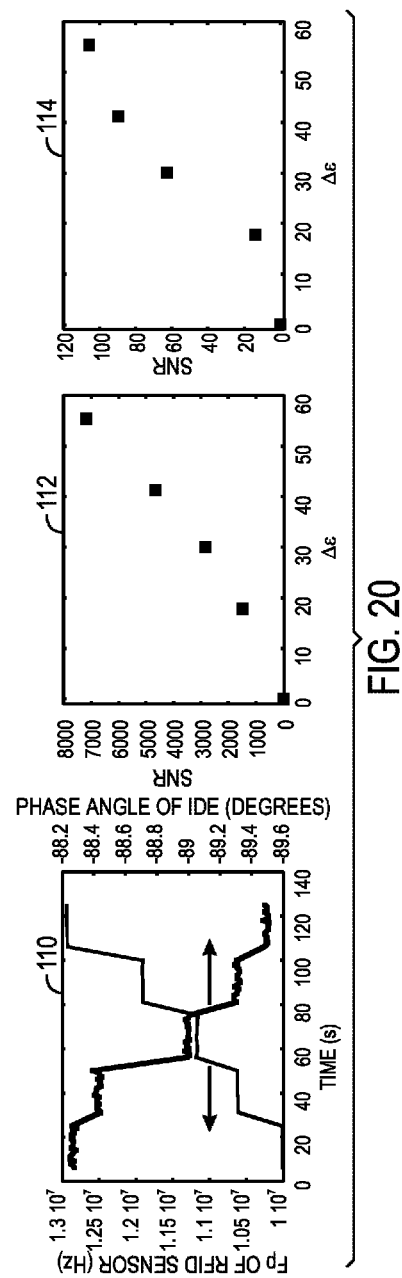

From the analysis of the collected data, it was observed that conventional impedance spectroscopy measurements have a much larger relative noise in the signal, as illustrated by plot 110 of FIG. 20. To evaluate the SNR of sensor response, data was processed, as shown in plots 112 (frequency shift response of the LCR sensor) and 114 (phase shift response of conventional impedance spectroscopy sensor) of FIG. 20. Compared to the conventional impedance spectroscopy (plot 114), the resonant LCR sensor (plot 112) provided an at least 100-fold enhancement in the SNR over the smallest measured range of Ac with the corresponding improvement of detection limit of dielectric constant determinations.

EXAMPLE 10

Improvement of Selectivity of Sensing of Vapors of Same Dielectric Constant Using Power Modulation Embodiments of the invention also provide the ability to discriminate between vapors of similar dielectric constant at room temperature, as illustrated in the experimental data of FIGS. 21-25. The selected vapors for this experiment were 1-pentanol (vapor 1), paraldehyde (vapor 2), and salicylaldehyde (vapor 3). The discrimination was achieved using power modulation. An interdigital chip served as a complementary sensor that was attached across an antenna of a passive RFID tag. The chip was 2×2 mm$^2$ and had gold electrodes that were 10 µm wide and 10 µm spaced from each other. A sensing film made of octanethiol-capped Au nanoparticles, manufactured by Sigma-Aldrich®, product #660426, was applied onto a sensor chip by drop casting. The power of operation of the RFID sensor was controlled from −10 dBm to 0 dBm.

Figure 21:
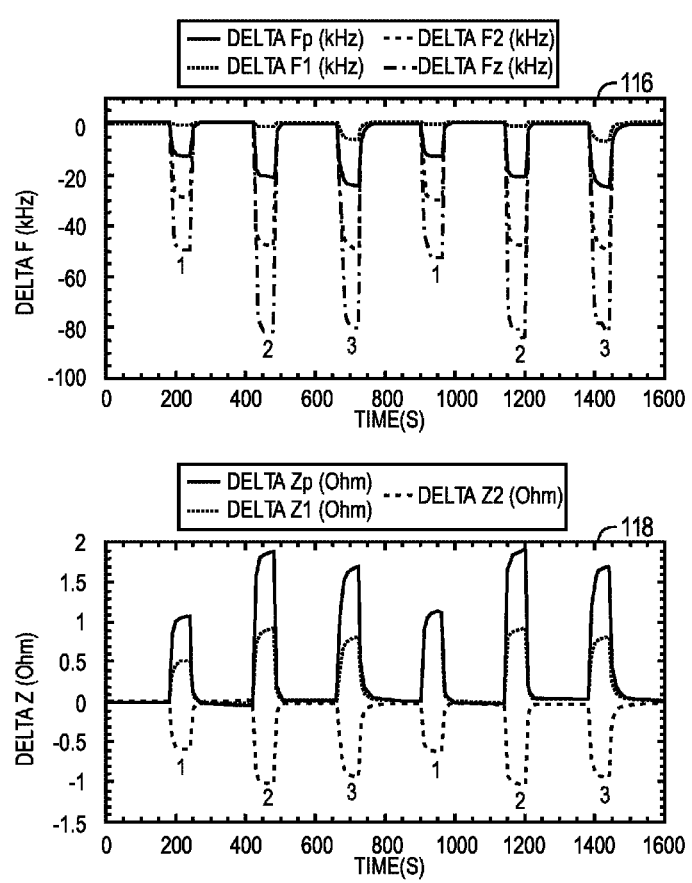
FIGS. 21-25 illustrate test data demonstrating improved selectivity of sensing of vapors of the same dielectric constant using power modulation.
Figure 22:
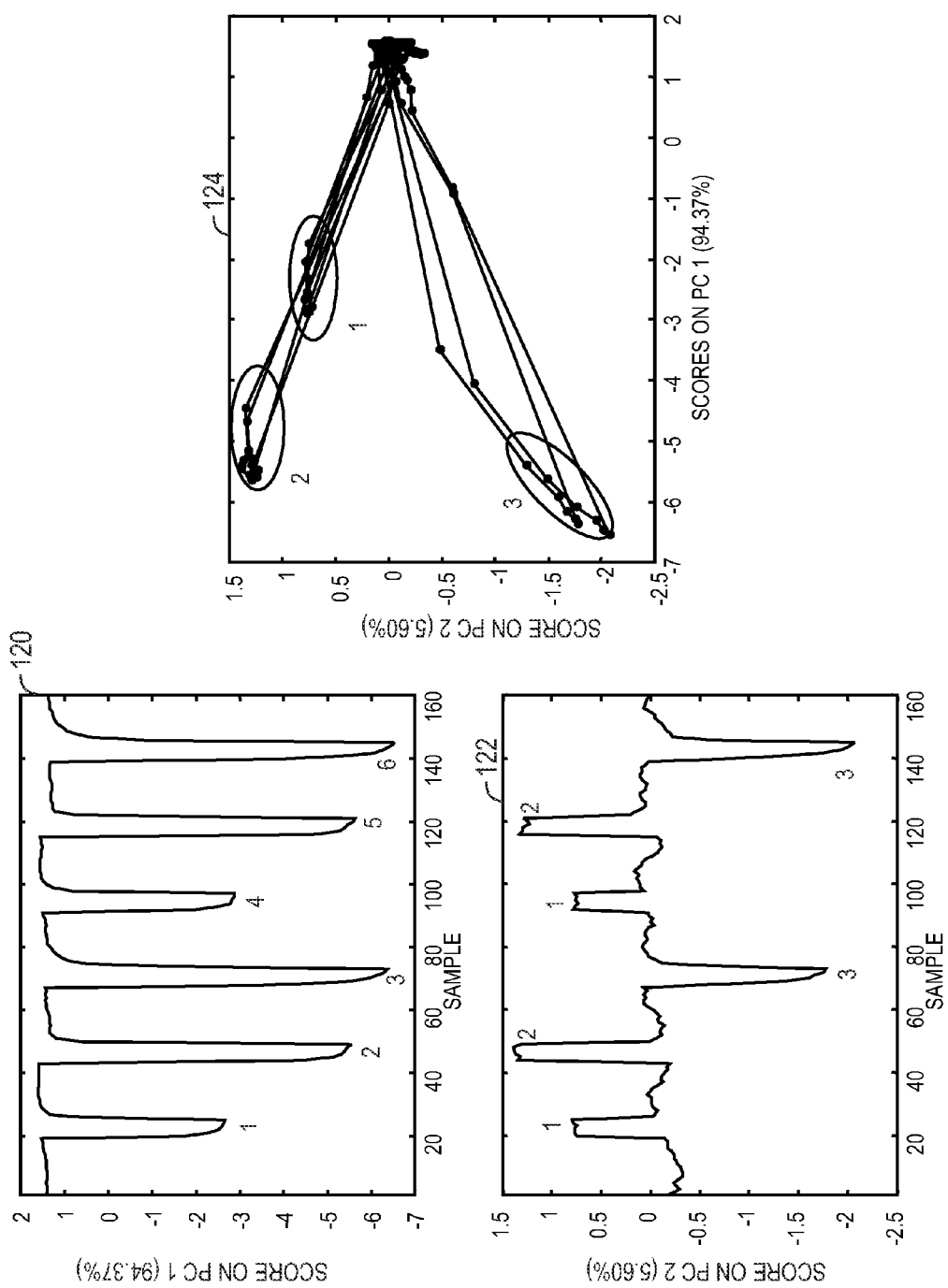

Plots 116 and 118 of FIG. 21 illustrate individual Fp, F1, F2, Fz, Zp, Z1 and Z2 responses upon a −10 dBm excitation. Results of PCA analysis of these responses is illustrated in FIG. 22. Plots 120 and 122 show the first two principal components as a function of measurement time. Plot 124 shows the first two principal components demonstrating the difficulties in discriminating between vapors 1 and 2.

Figure 23:
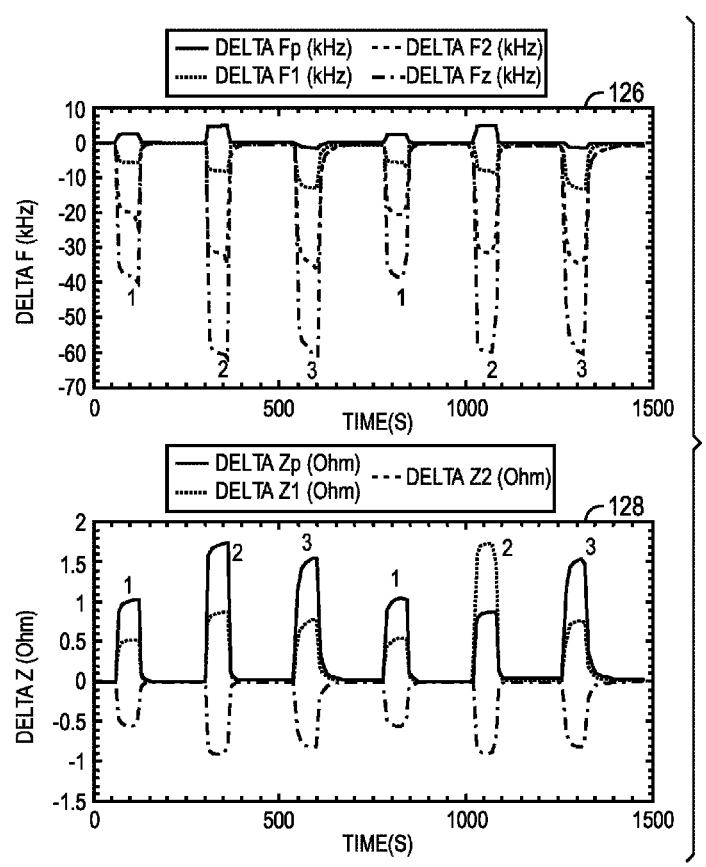
Figure 24:
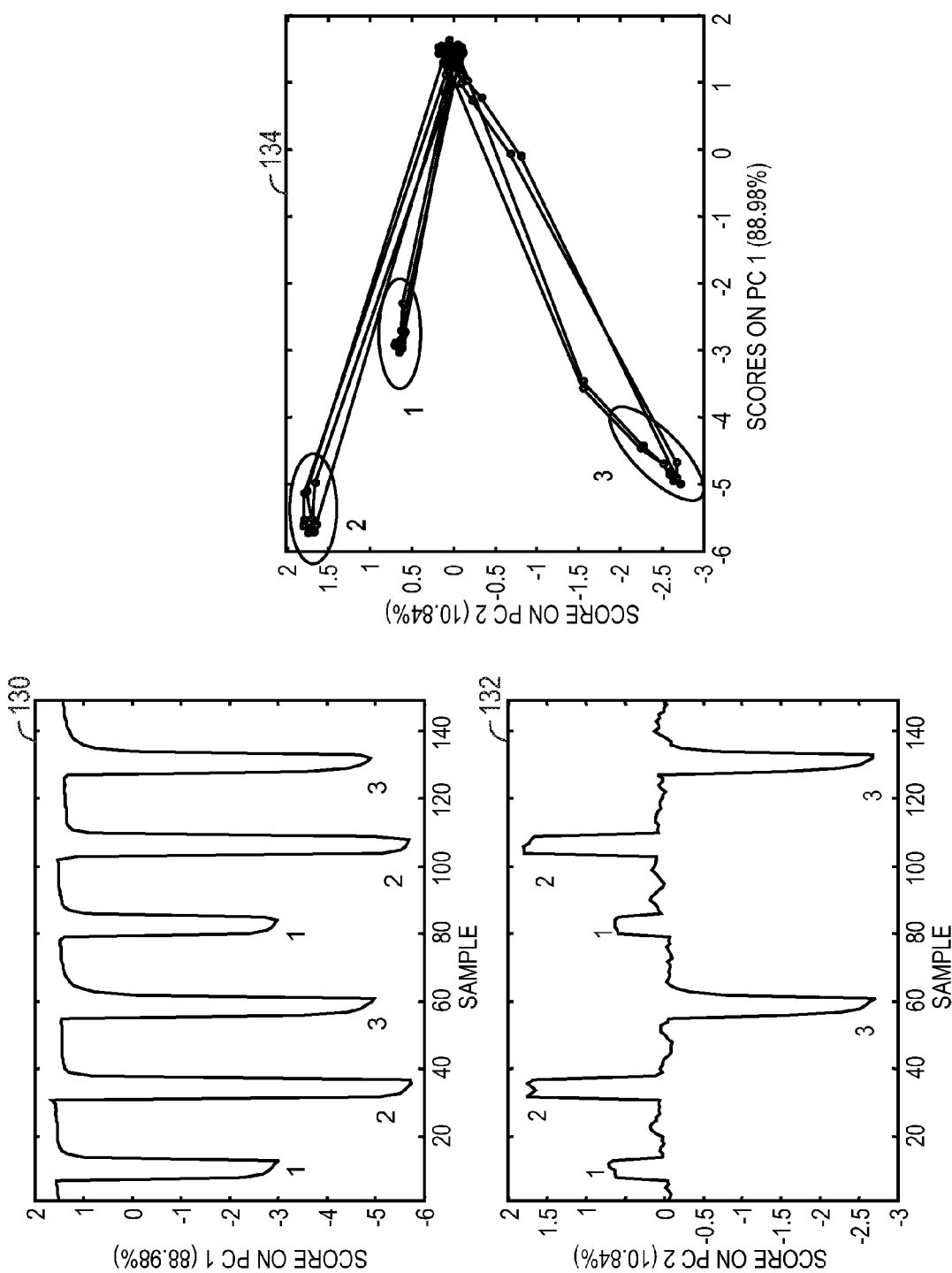

Plots 126 and 128 of FIG. 23 illustrate individual Fp, F1, F2, Fz, Zp, Z1 and Z2 responses upon a 0 dBm excitation. Results of PCA analysis of these responses is illustrated in FIG. 24. Plots 130 and 132 show of the first two principal components as a function of measurement time. Plot 134 shows the first two principal components demonstrating the discrimination between vapors 1, 2, and 3.

Figure 25:
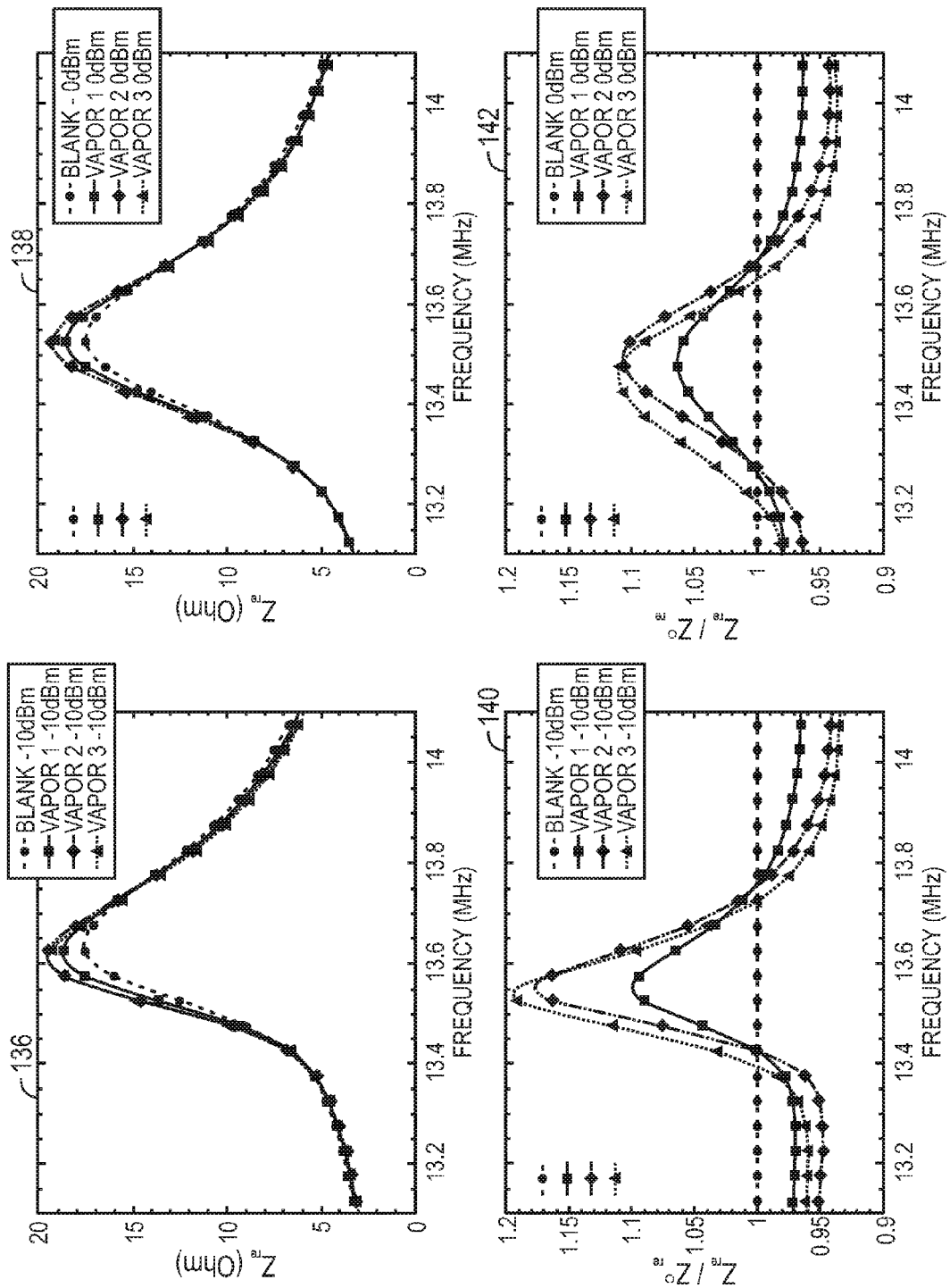

FIG. 25 illustrates examples of changes of the resonance impedance spectral profiles of the passive RFID sensor upon −10 and 0 dBm excitation when the sensor was exposed to a blank gas without tested vapors and to vapors 1, 2, and 3. Plots 136 and 138 of FIG. 25 illustrate the changes in the real part of the resonance impedance spectra $Z_{re}(f)$ at −10 and 0 dBm excitation, respectively. To illustrate the details of the spectral changes, the spectra of sensor response to vapors 1, 2, and 3 were normalized by the relevant spectra $Z°_{re}(f)$ of the sensor exposed to a blank gas without tested vapors. Plots 140 and 142 illustrate these normalized spectra $Z_{re}/Z°_{re}$ at −10 and 0 dBm excitation, respectively. Plots 140 and 142 conclusively demonstrate that the vapor-induced resonance impedance is significantly changed upon changes in the excitation power from −10 dBm to 0 dBm. These changes provide the ability to discriminate between all three vapors at an appropriately selected level of excitation power for the RFID sensor as shown in plot 134 of FIG. 24.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensor, comprising:
a single transducer having transducer electrodes, wherein the single transducer has a multivariate output to independently detect effects of different environmental parameters on the sensor; and
a sensing material disposed on the single transducer and having a preserved magnitude of response to an analyte over a broad concentration range of an interferent, wherein the sensing material is configured to have a preserved magnitude of response for at least six different analyte fluids from an analyzed fluid mixture, and wherein the sensor is configured to sense a first fluid in the analyzed fluid mixture in the presence of a second fluid in the analyzed fluid mixture, and wherein a concentration of the second fluid is at least 1 million times greater than a concentration of the first fluid.

2. The sensor of claim 1, wherein the sensing material has multiple response mechanisms to analytes and interferents.

3. The sensor of claim 2, wherein the response mechanisms of the sensing material are related to the changes of dielectric constant, resistance, and swelling of the sensing material, and wherein the changes are not fully correlated with each other and produce different patterns upon exposure to individual fluids and their mixtures.

4. The sensor of claim 1, wherein the single transducer comprises an inductor-capacitor-resistor (LCR) transducer.

5. The sensor of claim 4, wherein the LCR transducer comprises an RFID transducer with an integrated circuit chip.

6. The sensor of claim 4, wherein the sensor has multiple components of LCR response from the LCR transducer, and wherein the multiple components of LCR response originate from one or more factors affecting the LCR transducer.

7. The sensor of claim 6, wherein the one or more factors comprise resistance and capacitance of the sensing material, resistance and capacitance between the transducer electrodes and the sensing material, and resistance and capacitance between a transducer substrate and the sensing material.

8. A sensor, comprising:
a single transducer having transducer electrodes, wherein the single transducer has a multivariate output to independently detect effects of different environmental parameters on the sensor; and
a composite sensing material disposed on the single transducer and having a preserved magnitude of response to an analyte over a broad concentration range of an interferent, wherein the composite sensing material comprises a plurality of individual sensing materials that are homogeneously or inhomogeneously mixed or locally patterned over specific portions of the single transducer such that each of the plurality of individual sensing materials is arranged to respond to analytes by predominantly different response mechanisms, and wherein the composite sensing material is phase-separate due to hydrophylic/hydrophobic interactions or mutual immiscibility, formed as sectors of individual materials deposited adjacent to each other onto a single sensor, or formed as layers of individual materials deposited on top of each other onto a single sensor.

9. The sensor of claim 8, wherein the single transducer comprises an inductor-capacitor-resistor (LCR) transducer.

10. The sensor of claim 8, wherein the sensor is configured to sense the analyte when a concentration of the interferent is at least ten times greater than a concentration of the analyte.

11. The sensor of claim 10, wherein the interferent comprises water vapor.

12. A sensor, comprising:
a single transducer having transducer electrodes, wherein the single transducer has a multivariate output to independently detect effects of different environmental parameters on the sensor;
a sensing material disposed on the single transducer and having a preserved magnitude of response to an analyte over a broad concentration range of an interferent; and
an integrated circuit device comprising a diode rectifier, a network analyzer, a first processor, and a second processor;

wherein the integrated circuit device is configured to control selectivity of the sensor response;

wherein the diode rectifier is configured to power the sensor to at least two power levels to affect at least one of the dipole moment, the dielectric constant, and the temperature of the sensing material;

wherein the network analyzer is configured to collect spectral parameters of the sensor response at the at least two power levels;

wherein the first processor is configured to perform multivariate analysis of the spectral parameters from combined impedance spectral profiles of the sensor at the different power levels; and wherein the first processor or the second processor are configured to calculate values of environmental parameters to which the sensor is exposed from data produced by performing the multivariate analysis.

13. The sensor of claim 12, wherein the first processor is configured to perform multivariate analysis of the spectral parameters such that differences in the spectral profiles at each of the at least two different power levels are pronounced in different values of Fp, F1, F2, Fz, Zp, Z1, Z2, and calculated values of C and R.

14. The sensor of claim 12, wherein the at least two power levels are in a range from −50 dBm to +40 dBm.

15. The sensor of claim 12, wherein the first processor or the second processor is configured to calculate a concentration of the analyte in the presence of the interferent.

16. The sensor of claim 12, wherein the multivariate analysis comprises principal components analysis, canonical correlation analysis, regression analysis, nonlinear regression analysis, discriminate function analysis, multidimensional scaling, linear discriminate analysis, logistic regression, neural network analysis, or any combination thereof.

17. The sensor of claim 12, wherein a first power level of the at least two power levels is in a range of approximately −40 dBm to −1 dBm, and wherein a second power level of the at least two power levels is in a range of approximately 0 dBm to 40 dBm.

18. The sensor of claim 17, wherein the diode rectifier is configured to power the sensor to the at least two power levels on a time scale which is at least 5 times faster than dynamic changes in measured environmental parameters.

* * * * *